US007932261B2

(12) United States Patent
Baxter et al.

(10) Patent No.: US 7,932,261 B2
(45) Date of Patent: Apr. 26, 2011

(54) MACROCYCLE DERIVATIVES USEFUL AS INHIBITORS OF β-SECRETASE (BACE)

(75) Inventors: Ellen W. Baxter, Glenside, PA (US); François P. Bischoff, Vosselaar (BE); Hans De Winter, Schllde (BE); Chih Yung Ho, Lansdale, PA (US); Yifang Huang, Lansdale, PA (US); Michael H. Parker, Chalfont, PA (US); Allen B. Reitz, Lansdale, PA (US); Charles H. Reynolds, Lansdale, PA (US); Eric D. Strobel, Warrington, PA (US)

(73) Assignee: Janssen Pharmaceutica NV, Beerse (BE)

( * ) Notice: Subject to any disclaimer, the term of this patent is extended or adjusted under 35 U.S.C. 154(b) by 266 days.

(21) Appl. No.: 11/671,732

(22) Filed: Feb. 6, 2007

(65) Prior Publication Data

US 2007/0232630 A1    Oct. 4, 2007

Related U.S. Application Data

(60) Provisional application No. 60/765,624, filed on Feb. 6, 2006.

(51) Int. Cl.
  C07D 487/04   (2006.01)
  A61K 31/517   (2006.01)
(52) U.S. Cl. .................................... 514/266.4; 540/456
(58) Field of Classification Search .................. 540/456; 514/266.4
  See application file for complete search history.

(56) References Cited

U.S. PATENT DOCUMENTS

| | | | |
|---|---|---|---|
| 3,138,595 A | 6/1964 | Osdene et al. |
| 4,001,237 A | 1/1977 | Partyka et al. |
| 4,675,047 A | 6/1987 | Serban et al. |
| 4,739,056 A | 4/1988 | Venuti et al. |
| 4,761,416 A | 8/1988 | Fried et al. |
| 5,387,742 A | 2/1995 | Cordell |
| 5,580,003 A | 12/1996 | Malone et al. |
| 5,612,486 A | 3/1997 | McConlogue et al. |
| 5,672,805 A | 9/1997 | Neve |
| 5,720,936 A | 2/1998 | Wadsworth et al. |
| 5,811,633 A | 9/1998 | Wadsworth et al. |
| 5,850,003 A | 12/1998 | McLonlogue et al. |
| 5,877,015 A | 3/1999 | Hardy et al. |
| 5,877,399 A | 3/1999 | Hsiao et al. |
| 6,037,521 A | 3/2000 | Sato et al. |
| 6,071,903 A | 6/2000 | Albright et al. |
| 6,184,435 B1 | 2/2001 | Benson et al. |
| 6,187,922 B1 | 2/2001 | Geen et al. |
| 6,211,428 B1 | 4/2001 | Singh et al. |
| 6,340,783 B1 | 1/2002 | Snow |
| 7,531,545 B2 | 5/2009 | Baxter et al. |
| 2004/0087548 A1 | 5/2004 | Salvati et al. |
| 2004/0209905 A1 | 10/2004 | Kubo et al. |
| 2005/0171111 A1 | 8/2005 | Angibaud et al. |
| 2006/0074105 A1 | 4/2006 | Ware, Jr. et al. |
| 2006/0178383 A1 | 8/2006 | Bischoff et al. |
| 2007/0232642 A1 | 10/2007 | Baxter et al. |
| 2008/0194624 A1 | 8/2008 | Baxter et al. |
| 2009/0227581 A1 | 9/2009 | Baxter et al. |
| 2009/0227627 A1 | 9/2009 | Baxter et al. |

FOREIGN PATENT DOCUMENTS

| | | |
|---|---|---|
| EP | 04/06958 | 1/1991 |
| EP | 371564 | 7/1995 |
| EP | 1407774 | 4/2004 |
| JP | 63-196573 | 8/1988 |
| WO | 01/38315 | 5/2001 |
| WO | WO 01/38314 | 5/2001 |
| WO | 02/100399 | 12/2002 |
| WO | WO 2004/022523 | 3/2004 |
| WO | WO 2004/058686 | 7/2004 |
| WO | WO 2005/049585 | 6/2005 |
| WO | WO 2006/017836 | 2/2006 |
| WO | WO 2006/017844 | 2/2006 |
| WO | WO 2006/024932 | 3/2006 |
| WO | 2006/078577 | 7/2006 |
| WO | 2007/050612 | 5/2007 |
| WO | 2007/092846 | 8/2007 |
| WO | 2007/092854 | 8/2007 |

OTHER PUBLICATIONS

Larner, A.J.: "Secretases as Therapeutic Targets in Alzheimer's Disease: Patents 2000-2004". Expert Opinion On Therapeutic Patents, Ashley Publications, GB, vol. 14, No. 10, 2004, pp. 1403-1420, XP002404250.

Kienzle, F., et al. "1,5-Dihydroimdazoquinazoliones as Blood Platelet Aggregation Inhibitors", European Journal of Medicinal Chemistry, 17(6), 547-556, (1982).

Webb, T. Improved Synthesis of Symmetrical and Unsymmetrical 5,11-Methandibenzo'b.f.1,5-iazocines. Readily Available Inanoscale Structural Units, Journal of Organic Chemistry, vol. 55, No. 1, 1990, pp. 363-365.

Venuti, M., et al. Inhibitors of Cyclic AMP Phosphodiestrase 2 Structural Variations of N-Cyclohexyl-N-Methyl-4-(1,2,3,5-Tetrahydro-2-Oxoimidazo 2,1-B Quinazo-7-yl-Oxybutyramids J. Medicinal Chemistry, American Chemical Society, vol. 30, No. 2, 1987, pp. 303-318.

Patent Abstracts of Japan, vol. 16, No. 160 (P140) Apr. 20, 1992, JP 04 011255 (Fuji Photo Film Co. Ltd.) Jan. 16, 1992, p. 5, compound 20.

Office Action mailed Aug. 21, 2008 in U.S. Appl. No. 11/197,669.
Office Action mailed Apr. 29, 2009 in U.S. Appl. No. 11/197,669.
Office Action mailed May 30, 2008 in U.S. Appl. No. 11/197,608.
Office Action mailed Aug. 20, 2008 in U.S. Appl. No. 11/197,608.
Office Action mailed Apr. 30, 2009 in U.S. Appl. No. 11/197,608.
Office Action mailed May 29, 2008 in U.S. Appl. No. 11/197,615.
Office Action mailed Jan. 27, 2009 in U.S. Appl. No. 11/197,615.
Office Action mailed Jun. 19, 2009 in U.S. Appl. No. 11/671,681.
Office Action mailed Jun. 19, 2008 in U.S. Appl. No. 11/671,703.
Office Action mailed Aug. 20, 2008 in U.S. Appl. No. 11/671,703.

(Continued)

Primary Examiner — Bruck Kifle

(57) ABSTRACT

The present invention is directed to macrocycle derivatives, pharmaceutical compositions containing them and their use in the treatment of Alzheimer's disease (AD) and related disorders. The compounds of the invention are inhibitors of β-secretase, also known as β-site cleaving enzyme and BACE, BACE1, Asp2 and memapsin2.

8 Claims, No Drawings

OTHER PUBLICATIONS

Office Action mailed Feb. 12, 2009 in U.S. Appl. No. 11/671,703.
Office Action mailed Jun. 9, 2009 in U.S. Appl. No. 11/671,703.
Office Action mailed Sep. 10, 2009 in U.S. Appl. No. 12/362,020.
Citron, Trends in Pharm. Sci., vol. 25, Issue 2, Feb. 2004, 92-97.
Cole, et al., Molecular Neurodegeneration 2007, 2:22.
Database Caplus "Online!" Chemical Abstracts Service, Columbus, Ohio, US Ishikawa, Fumyoshi et al.: "Quinazolineacetic acid derivatives as platelet aggregation inhibitors". XP00236713, 1989.
Hamaguchi, et al., Cell. Mol. Life Sci. 63 (2006) 1538-1552.
Kienzle, F. et. al., Chemical Abstract, 1983, vol. 98, Abstract No. 143363, (or CAPLUS Accession No. 1983:143363).
Notice of Allowance dated Dec. 8, 2009 in U.S. Appl. No. 11/197,669.
Notice of Allowance dated Dec. 8, 2009 in U.S. Appl. No. 11/197,608.
Office Action dated Sep. 29, 2009 in U.S. Appl. No. 11/671,681.
El Mouedden, M. et al., (Johnson & Johnson Pharmaceutical Research and Development, Division of Janssen Pharmaceutica N.V., Turnhoutseweg 30, Beerse, Belg.), Development of a specific ELISA for the quantitative study of amino-terminally truncated beta-amyloid peptides,. Journal of Neuroscience Methods (2005), 145(1-2), pp. 97-105.
Ermolieff et al., Biochemistry, (2000) vol. 39, p. 12450.
Games, D. et al., (Athena Neurosciences, Inc., South San Francisco, CA, USA), Alzheimer-type neuropathology in transgenic mice overexpressing V717F β-amyloid precursor protein, Nature (London) (1995), 373(6514), pp. 523-527 (V717F mice).
Hsiao, K. et al., (Dep. Neurology, Univ. Minnesota, Minneapolis, MN, USA), Correlative memory deficits, Aβ elevation, and amyloid plaques in transgenic mice, Science (Washington, D. C.) (1996), 274(5284), pp. 99-102 (Tg2576 mice).
Lewczuk, P. et al., (Department of Psychiatry and Psychotherapy, Molecular Neurobiology Lab, University of Erlangen-Nuremberg, Erlangen, Germany), Neurochemical diagnosis of Alzheimer's dementia by CSF Aβ42, Aβ42/Aβ40 ratio and total tau, Neurobiology of Aging (2004), 25(3), pp. 273-281.
Lins, H. et al., (Department of Neurology, Otto-von-Guericke-University, Magdeburg, Germany), Immunoreactivities of amyloid β peptide(1-42) and total τ protein in lumbar cerebrospinal fluid of patients with normal pressure hydrocephalus, Journal of Neural Transmission (2004), 111(3), pp. 273-280.
Neve, R. L. et al., (Dep. Genetics, Harvard Medical School and McLean Hospital, Belmont, MA, USA), Transgenic mice expressing APP-C100 in the brain, Neurobiology of Aging (1996), 17(2), pp. 191-203 (APP-C100 mice).
Oddo, S. et al, (Department of Neurobiology and Behavior, University of California, Irvine, Irvine, CA, USA), Triple-transgenic model of Alzheimer's disease with plaques and tangles: Intracellular Aβ and synaptic dysfunction, Neuron (2003), 39(3), pp. 409-421 (APP Triple Transgenic Mice).
Olsson, A. et al., (Sahlgrenska University Hospital, Experimental Neuroscience Section, Institute of Clinical Neuroscience, Goteborg University, Moelndal, Sweden), Measurement of α- and β-secretase cleaved amyloid precursor protein in cerebrospinal fluid from Alzheimer patients, Experimental Neurology (2003), 183(1), pp. 74-80.
Ruberti et al., (Neuroscience Program, International School for Advanced Studies (SISSA), Trieste, Italy), Phenotypic knockout of nerve growth factor in adult transgenic mice reveals severe deficits in basal forebrain cholinergic neurons, cell death in the spleen, and skeletal muscle dystrophy, Journal of Neuroscience (2000), 20(7), pp. 2589-2601 (AD11 mice).
Schoonenboom, N.S. et al., Amyloid β 38, 40, and 42 species in cerebrospinal fluid: More of the same?, Annals of Neurology (2005), 58(1), pp. 139-142.
Sirinathsinghji, D. J. S. (Merck Sharp and Dohme Research Laboratories, Neuroscience Research Centre, Essex, UK.), Transgenic mouse models of Alzheimer's disease, Biochemical Society Transactions (1998), 26(3), pp. 504-508.
Van Leuven, F. (Experimental Genetics Group, Center for Human Genetics, Flemish Institute for Biotechnology (VIB), K.U.Leuven, Louvain, Belg.), Single and multiple transgenic mice as models for Alzheimer's disease, Progress in Neurobiology (Oxford) (2000), 61(3), pp. 305-312.
Vanderstichele, H. et al., (Innogenetics NV, Ghent, Belg.), Standardization of measurement of β-amyloid(1-42) in cerebrospinal fluid and plasma, Amyloid (2000), 7(4), pp. 245-258.
Wahlund, L.-O et al., (Karolinska Institute, Section of Geriatric Medicine, department of Clinical Neuroscience and Family Medicine, Huddinge University Hospital, Stockholm, Sweden), Cerebrospinal fluid biomarkers for disease stage and intensity in cognitively impaired patients, Neuroscience Letters (2003), 339(2), pp. 99-102.
Office Action mailed Sep. 29, 2009 in U.S. Appl. No. 11/671,681.
Notice of Allowance mailed Dec. 8, 2009 in U.S. Appl. No. 11/197,669.
Notice of Allowance mailed Dec. 8, 2009 in U.S. Appl. No. 11/197,608.
Notice of Allowance mailed Dec. 24, 2009 in U.S. Appl. No. 12/362,020.
Bakke, J. M.; Lorentzen, G. B. Acta Chem. Scand. B 1974, 28, 650.
Baumgarth, M.; Beier, N.; Gericke, R. J. Med. Chem. 1998, 41, 3736.
Burk, M. J.; Gross, M. F.; Martinez, J. P. J. Am. Chem. Soc. 1995, 117, 9375.
Deloux, L.; Srebnik, M. J. Org. Chem. 1994, 59, 6871.
Fernandez et al., Org. Biomol. Chem., 2003, 1, 767-771.
Ford et al., J. Med. Chem. 1985, 28, 164.
Hintermann, T.; Gademann, K.; Jaun, B. Seebach, D. Hely. Chim. Acta 1998, 81, 983.
Hu, Y.-Z., Zhang, G., and Thummel, R.P., Org. Lett., vol. 5, 2003, p. 2251.
Jung, M. E.; Lam, P. Y.-S.; Mansuri, M. M.; Speltz, L. M. J. Org. Chem. 1985, 50, 1087.
Jung, M.E. and Dansereau, S.M.K., Heterocycles, vol. 39, 1994, p. 767.
Katritzky, A.R., Chassaing, C., Toader D. And Gill, K., J. Chem. Research, (S), 1999, pp. 504-505.
Katritzky, A.R., Lang, H., Wang, Z., Zhang, Z. And Song, H., J. Org. Chem., 60, 1990, pp. 7619-7624.
Lhermitte, F.; Carboni, B. Synlett, 1996, 377.
Matsubara, S.; Otake, Y.; Hashimoto, Y.; Utimoto, K. Chem. Lett. 1999, 747.
Miyaura, N.; Suzuki, A. Chem. Rev. 1995, 95, 2457.
Osdene, Thomas S. et al. Journal of Medicinal Chemistry (1967), 10(2), 165-7.
Smrcina, M.; Majer, P.; Majerová, E.; Guerassina, T. A.; Eissenstat, M. A. Tetrahedron 1997, 53, 12867.
Suzuki, A. J. Organomet. Chem. 1999, 576, 147.
Takai, K.; Shinomiya, N.; Kaihara, H.; Yoshida, N.; Moriwake, T. Synlett 1995, 963.
Vetelino, M.G. and Coe, J.W., Tetrahedron Lett., 35(2), 1994, pp. 219-22.
Yang, D.; Yip, Y.-C.; Jiao, G.-S.; Wong, M.-K. Org. Synth. 2000, 78, 225.
Notice of Allowance mailed May 4, 2010 in U.S. Appl. No. 11/671,681.
Notice of Allowance mailed Aug. 23, 2010 in U.S. Appl. No. 11/671,681.
Notice of Allowance mailed Nov. 19, 2009 in U.S. Appl. No. 11/671,703.
Notice of Allowance mailed Mar. 17, 2010 in U.S. Appl. No. 11/671,703.
Office Action mailed May 29, 2008 in U.S. Appl. No. 11/197,669.
Office Action mailed Sep. 29, 2009 in U.S. Appl. No. 11/197,615.
Notice of Allowance mailed Apr. 19, 2010 in U.S. Appl. No. 11/197,615.
Notice of Allowance mailed Apr. 14, 2010 in U.S. Appl. No. 12/362,020.

MACROCYCLE DERIVATIVES USEFUL AS INHIBITORS OF β-SECRETASE (BACE)

CROSS REFERENCE TO RELATED APPLICATIONS

This application claims the benefit of U.S. Provisional Application 60/765,624, filed on Feb. 6, 2006, which is incorporated by reference herein in its entirety.

FIELD OF THE INVENTION

The present invention is directed to novel macrocycle derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin2.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibrillary tangles which are generated by hyperphosphorylation of tau protein and amyloid plaques which form by aggregation of β-amyloid$_{1\text{-}42}$ (Aβ$_{1\text{-}42}$) peptide. Aβ$_{1\text{-}42}$ forms oligomers and then fibrils, and ultimately amyloid plaques. The oligomers and fibrils are believed to be especially neurotoxic and may cause most of the neurological damage associated with AD. Agents that prevent the formation of Aβ$_{1\text{-}42}$ have the potential to be disease-modifying agents for the treatment of AD. Aβ$_{1\text{-}42}$ is generated from the amyloid precursor protein (APP), comprised of 770 amino acids. The N-terminus of Aβ$_{1\text{-}42}$ is cleaved by β-secretase (BACE), and then γ-secretase cleaves the C-terminal end. In addition to Aβ$_{1\text{-}42}$, γ-secretase also liberates Aβ$_{1\text{-}40}$ which is the predominant cleavage product as well as Aβ$_{1\text{-}38}$ and Aβ$_{1\text{-}43}$. Thus, inhibitors of BACE would be expected to prevent the formation of Aβ$_{1\text{-}42}$ as well as Aβ$_{1\text{-}40}$, Aβ$_{1\text{-}38}$ and Aβ$_{1\text{-}42}$ and would be potential therapeutic agents in the treatment of AD.

SUMMARY OF THE INVENTION

The present invention is directed to compounds of formula (I)

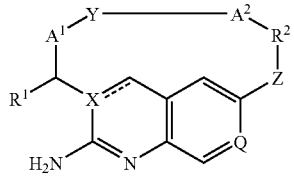

wherein

---- is a single or double bond;

X is selected from the group consisting of —N— and —C=;

Q is selected from the group consisting of =N— and =C(R$^4$)—; wherein R$^4$ is selected from the group consisting of hydrogen, halogen, C$_{1\text{-}4}$alkyl and C$_{1\text{-}4}$alkoxy; provided that when —C= is then Q is —C(R$^4$)=;

R$^1$ is selected from the group consisting of hydrogen, C$_{1\text{-}8}$alkyl, hydroxy substituted C$_{2\text{-}8}$alkyl, NR$^A$R$^B$ substituted —C$_{2\text{-}8}$alkyl, —C$_{1\text{-}4}$alkyl-O—C$_{1\text{-}4}$alkyl, cycloalkyl, heterocycloalkyl, —(C$_{1\text{-}4}$alkyl)-(cycloalkyl) and —(C$_{1\text{-}4}$alkyl)-(heterocycloalkyl); wherein R$^A$ and R$^B$ are each independently selected from the group consisting of hydrogen and C$_{1\text{-}4}$alkyl;

provided that when R$^1$ is hydroxy substituted C$_{2\text{-}8}$alkyl or NR$^A$R$^B$ substituted C$_{2\text{-}8}$alkyl, then the hydroxy or NR$^A$R$^B$ group is not bound to the alpha carbon (i.e. the hydroxy or NR$^A$R$^B$ group is not bound to the carbon atom bound directly to the carbon atom bound to the X and A$^1$ groups);

A$^1$ is selected from the group consisting of —C$_{1\text{-}6}$alkyl- and —C$_{2\text{-}6}$alkenyl-;

Y is selected from the group consisting of —N(R$^3$)—, —C(O)—N(R$^3$)— and —N(R$^3$)—C(O)—; provided that when X is =C— and Q is —C(R$^4$)=, then Y is selected from the group consisting of —C(O)—N(R$^3$)—;

wherein R$^3$ is selected from the group consisting of hydrogen, C$_{1\text{-}8}$alkyl, —C$_{1\text{-}4}$alkyl-OH, C$_{3\text{-}8}$cycloalkyl, —(C$_{1\text{-}5}$alkyl)-C$_{3\text{-}8}$cycloalkyl and 5 to 6 membered heterocycloalkyl; wherein the cycloalkyl or heterocycloalkyl is optionally substituted with one or more substituents independently selected from the group consisting of hydroxy, carboxy and —C(O)O—C$_{1\text{-}4}$alkyl;

A$^2$ is a absent or is selected from the group consisting of —C$_{1\text{-}6}$alkyl-, —C$_{2\text{-}6}$alkenyl- and —C$_{1\text{-}6}$alkyl-O—;

R$^2$ is selected from the group consisting of -phenyl-, -tetrahydronaphthyl- and -indanyl-;

Z is absent or is —O—;

and a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the β-secretase enzyme in a subject in need thereof, comprising administering to the subject a therapeutically effective amount of any of the compounds or pharmaceutical compositions described above.

Further exemplifying the invention are methods of inhibiting the β-secretase enzyme, comprising administering to a subject in need thereof a therapeutically effective amount of any of the compounds or pharmaceutical compositions described above.

An example of the invention is a method of treating a disorder selected from the group consisting of Alzheimer's disease (AD), mild cognitive impairment, senility, dementia, dementia with Lewy bodies, Down's syndrome, dementia associated with stroke, dementia associated with Parkinson's disease and dementia associated with beta-amyloid, preferably Alzheimer's disease, in a subject in need thereof comprising administering to the subject an effective amount of any of the compounds or pharmaceutical compositions described above.

Another example of the invention is the use of any of the compounds described above in the preparation of a medicament for treating: (a) Alzheimer's Disease (AD), (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I)

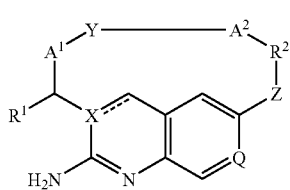

(I)

and pharmaceutically acceptable salts thereof, wherein X, $R^1$, $A^1$, Y, A, $R^2$, Z and Q are as herein defined. The compounds of formula (I) are inhibitors of the β-secretase enzyme (also known as β-site cleaving enzyme, BACE, BACE1, Asp2 or memapsin2), and are useful in the treatment of Alzheimer's disease (AD), mild cognitive impairment (MCI), senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the present invention, X is —N— and Q is =N—. In another embodiment of the present invention X is —N— and Q is =C($R^4$)—. In another embodiment of the present invention X is —C= and Q is =C($R^4$)—.

In an embodiment of the present invention, X is selected from the group consisting of —N— and =C—. In another embodiment of the present invention, X is —N—.

In an embodiment of the present invention, Q is selected from the group consisting of —N= and =C($R^4$)—. In another embodiment of the present invention, Q is selected from the group consisting of =CH— and —N=. In another embodiment of the present invention, Q is =C($R^4$)—.

In an embodiment of the present invention, $R^4$ is selected from the group consisting of hydrogen, halogen, $C_{1-4}$alkyl and $C_{1-4}$alkoxy. In another embodiment of the present invention, $R^4$ is selected from the group consisting of hydrogen, halogen and $C_{1-4}$alkoxy. In another embodiment of the present invention, $R^4$ is selected from the group consisting of hydrogen, fluoro and methoxy.

In an embodiment of the present invention, $R^1$ is selected from the group consisting of hydrogen, $C_{1-4}$alkyl, —$C_{1-4}$alkyl-O—$C_{1-4}$alkyl, cycloalkyl, —$C_{1-4}$alkyl-(cycloalkyl), saturated heterocycloalkyl and —$C_{1-4}$alkyl-(saturated heterocycloalkyl). In another embodiment of the present invention, $R^1$ is selected from the group consisting of hydrogen, $C_{1-4}$alkyl, $C_{3-8}$cycloalkyl and 5 to 7 membered, saturated heterocycloalkyl.

In another embodiment of the present invention, $R^1$ is selected from the group consisting of hydrogen, isopropyl, (R)-isopropyl, (S)-isopropyl, cyclohexyl, (S)-cyclohexyl, (R)-cyclohexyl, tetrahydropyranyl, (S)-tetrahydropyranyl and (R)-tetrahydropyranyl. In another embodiment of the present invention, $R^1$ is selected from the group consisting of hydrogen, (S)-isopropyl, (S)-cyclohexyl, (R)-cyclohexyl and (S)-tetrahydropyranyl. In another embodiment of the present invention, $R^1$ is selected from the group consisting of (S)-isopropyl, (S)-cyclohexyl and cyclohexyl.

In an embodiment of the present invention, $A^1$ is selected from the group consisting of —$C_{1-4}$alkyl- and $C_{2-4}$alkenyl. In another embodiment of the present invention, $A^1$ is selected from the group consisting of —$CH_2$—, —$CH_2CH_2$—, —$CH_2CH_2CH_2$— and —$CH_2$—CH=CH—. In another embodiment of the present invention, $A^1$ is selected from the group consisting of —$CH_2CH_2$— and —$CH_2CH_2CH_2$—. In another embodiment of the present invention, $A^1$ is selected from the group consisting of —$CH_2CH_2$— and —$CH_2$—CH=CH—.

In an embodiment of the present invention, Y is selected from the group consisting of —N($R^3$)—, —C(O)—N($R^3$)— and —N($R^3$)—C(O)—. In another embodiment of the present invention, Y is selected from the group consisting of —N(cyclohexyl)-, —C(O)—NH—, —C(O)—N(—$CH_2$-cyclopropyl)-, —C(O)—N(cyclopentyl)-, —C(O)—N(cyclohexyl)-, —C(O)—N(4-tetrahydropyranyl)-, —C(O)—N(1-(3-hydroxy-n-propyl))-, —C(O)—N(4-ethoxy-carbonyl-cyclohexyl)-, —C(O)—N(4-carboxy-cyclohexyl)-, —C(O)—N(cis-4-carboxy-cyclohexyl)-, —C(O)—N(trans-4-carboxy-cyclohexyl)-, —C(O)—N(4-hydroxy-cyclohexyl)-, —C(O)—N(cis-4-hydroxy-cyclohexyl)-, —C(O)—N(trans-4-hydroxy-cyclohexyl)-, —NH—C(O)— and —N(cyclohexyl)-C(O)—.

In another embodiment of the present invention, Y is selected from the group consisting of —N(cyclohexyl)-, —C(O)—NH—, —C(O)—N(—$CH_2$-cyclopropyl)-, —C(O)—N(cyclopentyl)-, —C(O)—N(cyclohexyl)-, —C(O)—N(4-tetrahydropyranyl)-, —C(O)—N(1-(3-hydroxy-n-propyl))-, —C(O)—N(4-ethoxy-carbonyl-cyclohexyl)-, —C(O)—N(4-carboxy-cyclohexyl)-, —C(O)—N(cis-4-carboxy-cyclohexyl)-, —C(O)—N(trans-4-carboxy-cyclohexyl)-, —C(O)—N(4-hydroxy-cyclohexyl)-, —C(O)—N(cis-4-hydroxy-cyclohexyl)-, —C(O)—N(trans-4-hydroxy-cyclohexyl)- and —NH—C(O)—.

In another embodiment of the present invention, Y is selected from the group consisting of —C(O)—NH—, —C(O)—N(cyclohexyl)-, —C(O)—N(4-tetrahydropyranyl)-, —C(O)—N(cis-4-carboxy-cyclohexyl)-, —C(O)—N(trans-4-carboxy-cyclohexyl)- and —C(O—N(1-(3-hydroxy-n-propyl))-. In another embodiment of the present invention, Y is selected from the group consisting of —C(O)—N(cyclopentyl)-, —C(O)—N(cyclohexyl)-, —C(O)—N(cis-4-hydroxy-cyclohexyl)-, —C(O)—N(cis-4-hydroxy-cyclohexyl)- and —C(O)—N(—$CH_2$-cyclopropyl)-.

In an embodiment of the present invention, $R^3$ is selected from the group consisting of hydrogen, $C_{1-4}$alkyl, —$C_{1-4}$alkyl-OH, $C_{3-8}$cycloalkyl, —$C_{1-2}$alkyl-($C_{3-8}$cycloalkyl) and 5 to 6 membered, saturated heterocycloalkyl; wherein the cycloalkyl is optionally substituted with one to two substituents independently selected from hydroxy, carboxy or —C(O)O—$C_{1-4}$alkyl. In another embodiment of the present invention, $R^3$ is selected from the group consisting of hydrogen, $C_{1-4}$alkyl, —$C_{1-4}$alkyl-OH, $C_{3-8}$cycloalkyl, —$C_{1-2}$alkyl-($C_{3-8}$cycloalkyl) and 5 to 6 membered, saturated heterocycloalkyl; wherein the cycloalkyl is optionally substituted with one to two substituents independently selected from hydroxy, carboxy or —C(O)O—$C_{1-4}$alkyl.

In another embodiment of the present invention, $R^3$ is selected from the group consisting of hydrogen, —$C_{1-4}$alkyl-OH, $C_{5-7}$cycloalkyl, —$C_{1-2}$alkyl-($C_{3-8}$cycloalkyl) and 5 to 6 membered, saturated heterocycloalkyl; wherein the cycloalkyl is optionally substituted with a substituent selected from hydroxy, carboxy or —C(O)O—$C_{1-4}$alkyl. In another embodiment of the present invention, $R^3$ is selected from the group consisting of hydrogen, —$C_{1-4}$alkyl-OH, $C_{5-7}$cycloalkyl, —$C_{1-2}$alkyl-($C_{3-8}$cycloalkyl) and 5 to 6 membered, saturated heterocycloalkyl; wherein the cycloalkyl is optionally substituted with a substituent selected from hydroxy, carboxy or —C(O)O—$C_{1-4}$alkyl.

In an embodiment of the present invention, $A^2$ absent or is selected from the group consisting of —$C_{1-6}$alkyl-, $C_{2-6}$alkenyl and $C_{1-6}$alkyl-O—. In another embodiment of the present invention, $A^2$ absent or is selected from the group consisting of —$C_{1-4}$alkyl-, $C_{2-6}$alkenyl and $C_{1-4}$alkyl-O—.

In another embodiment of the present invention, $A^2$ absent or is selected from the group consisting of —$CH_2$—, —$CH_2CH_2$—, —$CH_2CH_2CH_2$—, —$CH_2CH_2CH_2CH=CH$—, —$CH_2CH_2$—O— and —$CH_2CH_2CH_2CH_2$—O—. In another embodiment of the present invention, $A^2$ is selected from the group consisting of —$CH_2CH_2$—, —$CH_2CH_2CH_2$— and —$CH_2CH_2$—O—.

In another embodiment of the present invention, $A^2$ is absent or is —$CH_2CH_2$—. In another embodiment of the present invention $A^2$ is —$CH_2CH_2$—. In another embodiment of the present invention, $A^2$ is absent.

In an embodiment of the present invention, $R^2$ is selected from the group consisting of -phenyl-, -tetrahydronaphthyl- and -indanyl-. In another embodiment of the present invention, $R^2$ is selected from the group consisting of -phenyl-, -tetrahydronaphthyl- and -indanyl-.

In another embodiment of the present invention, $R^2$ is selected from the group consisting of -phenyl- and -indanyl-.

In another embodiment of the present invention, $R^2$ is selected from the group consisting of 1,2-phenyl, 1,3-phenyl and 1,6-indanyl. In another embodiment of the present invention, $R^2$ is selected from the group consisting of 1,2-phenyl, 1,3-phenyl and 1,6-indanyl.

In another embodiment of the present invention, $R^2$ is selected from the group consisting of 1,3-phenyl and 1,6-indanyl. In another embodiment of the present invention, $R^2$ is 1,3-phenyl.

In an embodiment of the present invention Z is absent. In another embodiment of the present invention Z is —O—.

In additional embodiments, the present invention is directed to any single or subset of compounds of formula (I) selected from the group consisting of the compounds listed in Tables 1-3, below.

Additional embodiments of the present invention, include those wherein the substituents selected for one or more of the variables defined herein (e.g. wherein X, $R^1$, $A^1$, Y, A, $R^2$, Z, Q, etc.) are independently selected to be any individual substituent or any subset of substituents selected from the complete list as defined herein.

Representative compounds of the present invention are as listed in Tables 1 through 3, below. Unless otherwise noted, all compounds were prepared as mixtures of stereo-isomers. For substituent groups bound through two points within the structures in the Tables below, for example $A^1$, Y, $A^2$, etc., the substituent group is identified as it would be incorporated into the structure heading the table.

TABLE 1

Representative compounds of formula (I)

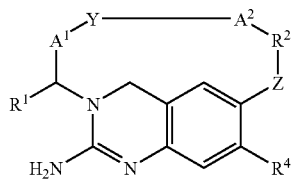

| ID No | $R^1$ | $A^1$ | Y | $A^2$ | $R^2$ | Z | $R^4$ |
|---|---|---|---|---|---|---|---|
| 1 | H | —(CH$_2$)$_2$— | —C(O)-N(cyclohexyl) | —(CH$_2$)$_3$— | 1,3-phenyl | O | H |
| 2 | (S)-cyclohexyl | —(CH$_2$)$_2$— | —C(O)-N(cyclohexyl) | —(CH$_2$)$_2$— | 1,3-phenyl | O | H |
| 3 | (S)-isopropyl | —CH$_2$— | —C(O)-N(cyclohexyl) | —(CH$_2$)$_3$— | 1,3-phenyl | O | H |
| 4 | H | —(CH$_2$)$_3$— | —C(O)-N(cyclohexyl) | —(CH$_2$)$_3$— | 1,3-phenyl | O | H |
| 5 | (R)-isopropyl | —CH$_2$— | —C(O)-N(cyclohexyl) | —(CH$_2$)$_3$— | 1,3-phenyl | O | H |
| 6 | (R)-cyclohexyl | —(CH$_2$)$_2$— | —C(O)-N(cyclohexyl) | —(CH$_2$)$_3$— | 1,3-phenyl | O | H |
| 7 | H | —(CH$_2$)$_2$— | —NH—C(O)— | —(CH$_2$)$_2$— | 1,3-phenyl | O | H |
| 8 | H | —(CH$_2$)$_2$— | —NH—C(O)— | —(CH$_2$)$_4$—O— | 1,2-phenyl | — | H |
| 9 | H | —(CH$_2$)$_2$— | —NH—C(O)— | —(CH$_2$)$_2$— | 1,3-phenyl | O | H |

TABLE 1-continued

Representative compounds of formula (I)

| ID No | R¹ | A¹ | Y | A² | R² | Z | R⁴ |
|---|---|---|---|---|---|---|---|
| 10 | H | —CH₂— | —N(C(O)-cyclohexyl)- | —(CH₂)₃— | 1,3-phenyl | O | H |
| 11 | H | —CH₂— | —NH—C(O)— | —(CH₂)₃—CH=CH— | 1,2-phenyl | — | H |
| 12 | H | —(CH₂)₂— | —NH—C(O)— | —CH₂— | 1,3-phenyl | O | H |
| 13 | (S)-isopropyl | —(CH₂)₂— | —C(O)-N(cyclohexyl)- | —(CH₂)₂— | 1,3-phenyl | O | H |
| 14 | (S)-cyclohexyl | —(CH₂)₂— | —C(O)-N(4-tetrahydro-pyranyl)- | —(CH₂)₂— | 1,3-phenyl | O | H |
| 15 | H | —CH₂— | -N(cyclohexyl)-C(O)— | —(CH₂)₂— | 1,3-phenyl | O | H |
| 16 | (S)-cyclohexyl | —CH₂— | —NH—C(O)— | —(CH₂)₂— | 1,3-phenyl | O | H |
| 17 | (S)-cyclohexyl | —(CH₂)₂— | —C(O)-N(cyclohexyl)- | —(CH₂)₂— | 1,3-phenyl | O | F |
| 18 | (S)-cyclohexyl | —(CH₂)₂— | —C(O)-N(cyclohexyl)- | —(CH₂)₂— | 1,3-phenyl | O | OCH₃ |
| 19 | (S)-cyclohexyl | —(CH₂)₃— | -N(cyclohexyl)- | —(CH₂)₃— | 1,3-phenyl | O | H |
| 20 | (S)-isopropyl | —(CH₂)₂— | —C(O)-N(4-tetrahydro-pyranyl) | —(CH₂)₂— | 1,3-phenyl | O | H |
| 21 | (S)-tetrahydro-pyranyl | —(CH₂)₂— | —C(O)—NH— | —(CH₂)₂— | 1,3-phenyl | O | H |
| 22 | (S)-isopropyl | —(CH₂)₂— | —C(O)-N(4-ethoxy-carbonyl-cyclohexyl) | —(CH₂)₂— | 1,3-phenyl | O | H |
| 23 | (S)-isopropyl | —(CH₂)₂— | —C(O)-N(cis-4-carboxy-cyclohexyl) | —(CH₂)₂— | 1,3-phenyl | O | H |
| 24 | (S)-isopropyl | —(CH₂)₂— | —C(O)-N(trans-4-carboxy-cyclohexyl) | —(CH₂)₂— | 1,3-phenyl | O | H |
| 25 | (S)-isopropyl | —(CH₂)₂— | —C(O)-N(1-(3-hydroxy-n-propyl))- | —(CH₂)₂— | 1,3-phenyl | O | H |
| 26 | (S)-isopropyl | —(CH₂)₂— | —C(O)-N(trans-4-hydroxy-cyclohexyl)- | —(CH₂)₂— | 1,3-phenyl | O | H |
| 27 | (S)-isopropyl | —(CH₂)₂— | —C(O)-N(cyclohexyl)- | —(CH₂)₂—O— | 1,3-phenyl | O | H |
| 28 | (S)-isopropyl | —(CH₂)₂— | —C(O)-N(4-ethoxy carbonyl-cyclohexyl)- | —(CH₂)₂— | 1,3-phenyl | O | H |
| 29 | (S)-cyclohexyl | —(CH₂)₂— | —C(O)-N(cis-4-carboxy-cyclohexyl)- | —(CH₂)₂— | 1,3-phenyl | O | H |
| 30 | (S)-cyclohexyl | —(CH₂)₂— | —C(O)-N(trans-4-carboxy-cyclohexyl)- | —(CH₂)₂— | 1,3-phenyl | O | H |
| 31 | (S)-isopropyl | —(CH₂)₂— | —C(O)—NH— | — | 2,7-napthyl | O | H |
| 35 | (S)-cyclohexyl | —(CH₂)₂— | —C(O)-N(cis-4-hydroxy-cyclohexyl)- | —(CH₂)₂— | 1,3-phenyl | O | H |
| 36 | (S)-isopropyl | —(CH₂)₂— | —C(O)-N(cyclohexyl)- | — | 1,6-indanyl | O | H |
| 41 | (S)-cyclohexyl | —(CH₂)₂— | —C(O)-N(cyclohexyl) | —(CH₂)₃— | 1,3-phenyl | O | H |

TABLE 2

Representative Compounds of Formula (I)

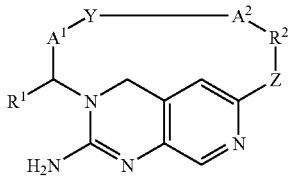

| ID No | R¹ | A¹ | Y | A² | R² | Z |
|---|---|---|---|---|---|---|
| 32 | (S)-cyclohexyl | —(CH$_2$)$_2$— | —C(O)-N(cyclohexyl)- | —(CH$_2$)$_2$— | 1,3-phenyl | O |
| 33 | (S)-cyclohexyl | —(CH$_2$)$_2$— | —C(O)-N(trans-4-carboxy-cyclohexyl)- | —(CH$_2$)$_2$— | 1,3-phenyl | O |
| 34 | (S)-cyclohexyl | —(CH$_2$)$_2$— | —C(O)-N(cis-4-hydroxy-cyclohexyl)- | —(CH$_2$)$_2$— | 1,3-phenyl | O |
| 37 | (S)-cyclohexyl | —(CH$_2$)$_2$— | —C(O)-N(cyclopentyl)- | —(CH$_2$)$_2$— | 1,3-phenyl | O |
| 38 | (S)-cyclohexyl | —(CH$_2$)$_2$— | —C(O)—N(—CH$_2$-cyclopropyl)- | —(CH$_2$)$_2$— | 1,3-phenyl | O |

TABLE 3

Representative Compounds of Formula (I)

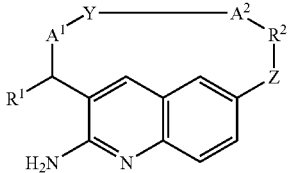

| ID No | R¹ | A¹ | Y | A² | R² | Z |
|---|---|---|---|---|---|---|
| 39 | cyclohexyl | —CH$_2$—CH=CH— | —C(O)-N(cyclohexyl)- | —(CH$_2$)$_2$— | 1,3-phenyl | O |
| 40 | cyclohexyl | —(CH$_2$)$_3$— | —C(O)-N(cyclohexyl)- | —(CH$_2$)$_2$— | 1,3-phenyl | O |

As used herein, unless otherwise noted, the term "halogen" shall mean chlorine, bromine, fluorine and iodine. Preferably, the halogen is fluoro or chloro. More preferably, the halogen is fluoro.

As used herein, unless otherwise noted, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl, isopentyl, hexyl, heptyl, octyl, nonyl, decyl, and the like. Similarly, the term "$C_{1-8}$alkyl" shall include straight and branched chains comprising one to eight carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "hydroxy substituted $C_{2-8}$alkyl" shall mean a straight or branched chain $C_{2-8}$alkyl, wherein the $C_{2-8}$alkyl is substituted with one or more, preferably one to three hydroxy groups, more preferably one to two hydroxy groups. Most preferably, the $C_{2-8}$alkyl group is substituted with one hydroxy group. Preferably, wherein the $C_{2-8}$alkyl group has a terminal carbon atom, the hydroxy group is bound at said terminal carbon atom.

As used herein, unless otherwise noted, the term "cycloalkyl" shall mean any stable monocyclic, bicyclic, polycyclic, bridged or spiro-bound, saturated ring system. Suitable examples include, but are not limited to, cyclopropyl, cyclobutyl, cyclopentyl, cyclohexyl, cycloheptyl, cyclooctyl, norboranyl, adamantyl, spiropentane, 2,2,2-bicyclooctyl, and the like. Unless otherwise noted, "cycloalkyl" groups do not contain N, O or S heteroatoms.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure. Preferably, the heterocycloalkyl is a saturated ring structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, tetrahydropyranyl, azepinyl, 2,3-dihydro-1,4-benzodioxanyl, and the like. Preferred heterocycloalkyl groups include piperidinyl, morpholinyl, tetrahydropyranyl and azepinyl.

As used herein, the notation "*" shall denote the presence of a stereogenic center.

When a particular group is "substituted" (e.g., cycloalkyl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, CH$_2$=CH—CH$_2$—, and the like; amides—groups of the formula —C(O)—R' wherein R' is for example methyl, phenyl, trifluoromethyl, and the like; N-sulfonyl derivatives—groups of the formula —SO$_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1999.

As used herein, unless otherwise noted, the term "oxygen protecting group" shall mean a group which may be attached to an oxygen atom to protect said oxygen atom from participating in a reaction and which may be readily removed following the reaction. Suitable examples include, but are not limited to methyl, benzyl, trimethylsilyl, tert-butyldimethylsilyl, acetate, 1-ethoxyethyl, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-(C$_1$-C$_6$alkyl)-aminocarbonyl-(C$_1$-C$_6$alkyl)-" substituent refers to a group of the formula

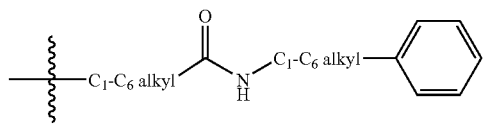

One skilled in the art will recognize that some substituent groups are bivalent (i.e. bound through two points of attachment), for example the substituent groups of A$^1$, A$^2$, Y, R$^2$, Z, and the like, in the compounds of formula (I) as described herein. One skilled in the art will further recognize that the bivalency of these groups is defined by the two bond indicators—i.e. dashes—in the listing of said groups. For example, in the definition of A$^1$, the group —C$_{1-4}$-alkyl- is intended to mean an alkyl chain comprising one to four carbon atoms, wherein the chain is bivalent. Similarly, the R$^2$ group -phenyl- is intended that the -phenyl- group is bivalent and therefore bound into the compound of formula (I) through any two carbon atoms of the phenyl group.

Abbreviations used in the specification, particularly the Schemes and Examples, are as follows:
Ac=Acetyl (i.e. —C(O)—CH$_3$)
AD=Alzheimer's Disease
APP=Amyloid Precursor Protein
BACE=β-amyloid site cleaving enzyme
Cbz=Carbobenzyloxy
DCE=Dichloroethane
DCM=Dichloromethane
DIPEA or DIEA=Diisopropylethylamine
DMA=N,N-Dimethylacetamide
DMF=N,N-Dimethylformamide
DMSO=Dimethylsulfoxide
EDCl or EDC=1-(3-Dimethylaminopropyl)3-ethylcarbodiimide hydrochloride
EtOAc=Ethyl acetate
EtOH=Ethanol
HBTU=O-Benzotriazol-1-yl-N, N, N',N'-tetramethyluronium hexafluorophosphate
HEPES=4-(2-Hydroxyethyl)-1-piperazine Ethane Sulfonic Acid
HOBT or HOBt=1-Hydroxybenzotriazole
HPLC=High Pressure Liquid Chromatography
LAH=Lithium Aluminum Hydride
LC/MS=Liquid Chromatography/Mass Spectrometry
LHMDS=Lithium hexamethylisilazide
MCI=Mild Cognitive Impairment
MeOH=Methanol
NaBH(OAc)$_3$=Sodium triacetoxyborohydride
NH$_4$OAc=Ammonium Acetate
NMR=Nuclear Magnetic Resonance
OM99-2=4-amino-4-{1-[2-carbamoyl-1-(4-{1-[3-carboxy-1-(1-carboxy-2-phenyl-ethylcarbamoyl)-propylcarbamoyl]-ethylcarbamoyl}-2-hydroxy-1-isobutyl-pentylcarbamoyl)-ethylcarbamoyl]-2-methyl-propylcarbamoyl}-butyric acid
Pd—C or Pd/C=Palladium on Carbon Catalyst
t-BOC or Boc=Tert-Butoxycarbonyl
TEA=Triethylamine
TFA=Trifluoroacetic Acid THF=Tetrahydrofuran
TLC=Thin Layer Chromatography The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography or recrystallization. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1999. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethane-sulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) wherein X is —N—, Q is —CH═, Y is —C(O)—N($R^3$)—, $R^3$ is other than hydrogen, $R^2$ is 1,3-phenyl and Z is —O— may be prepared according to the process outlined in Scheme 1.

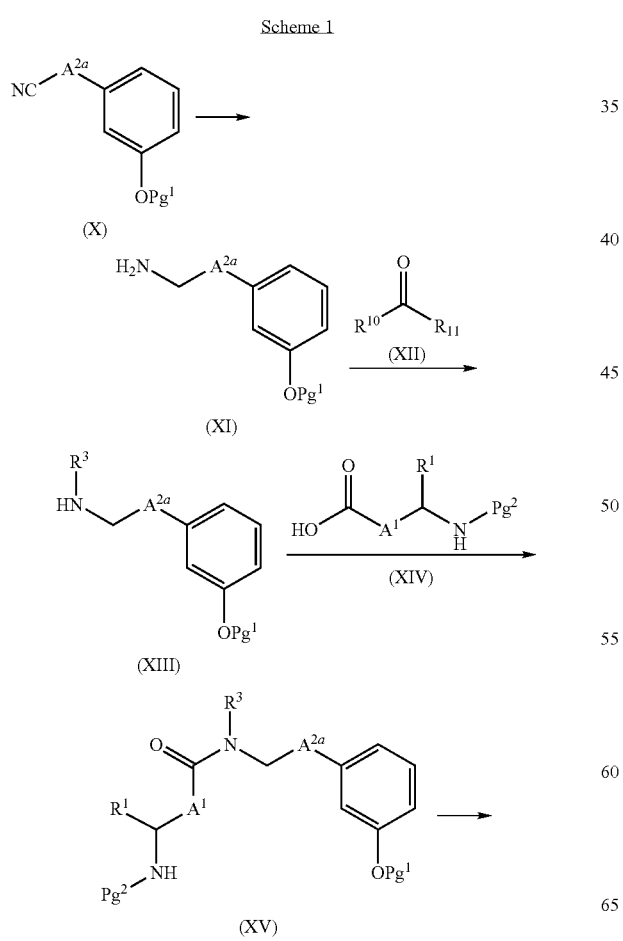
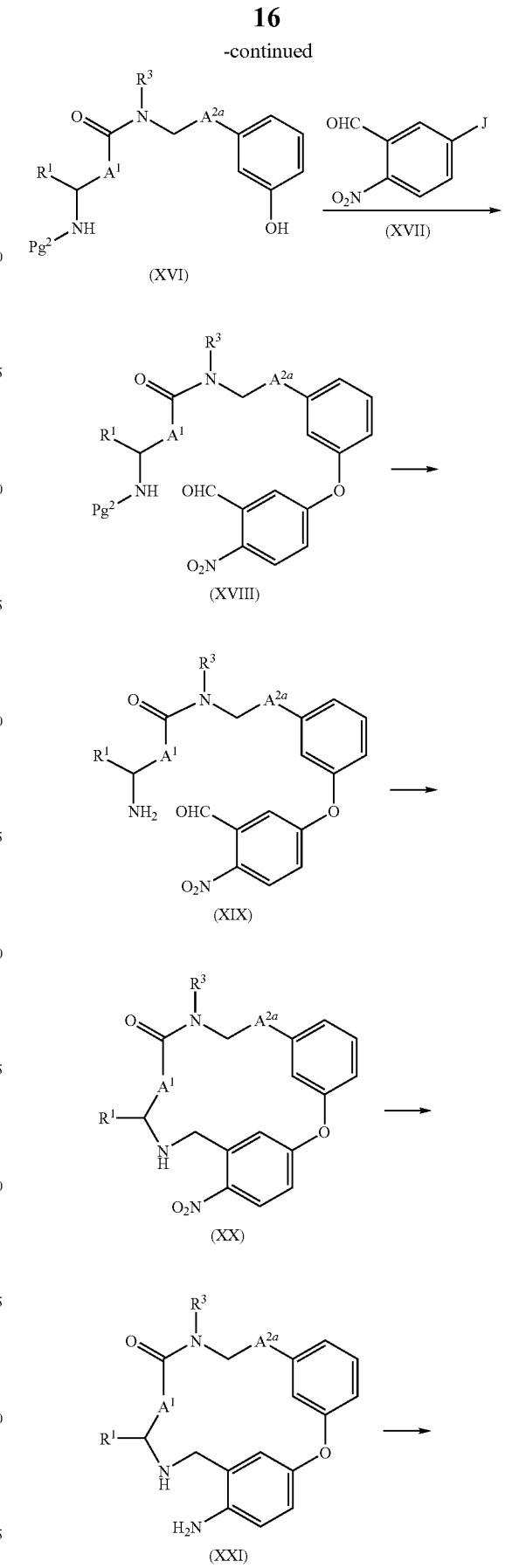

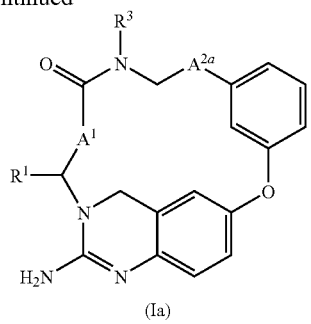

(Ia)

Accordingly, a suitably substituted compound of formula (X), wherein $A^{2a}$ represents the desired $A^2$ spacer absent a —$CH_2$— group on the portion of the $A^2$ group bound to the Y group (for example, wherein $A^2$ in the desired compound of formula (I) is —$CH_2$—$CH_2$—$CH_2$—, then $A^{2a}$ is —$CH_2$—$CH_2$—; wherein $A^2$ in the desired compound of formula (I) is —$CH_2$—CH=CH—, then $A^{2a}$ is —CH=CH—; and so forth) and wherein $Pg^1$ is a suitable oxygen protecting group such as benzyl, trialkylsilyl, and the like, preferably benzyl, a known compound or compound prepared by known methods, is reacted with a reducing agent such as borane-tetrahydrofuran, lithium aluminum hydride, and the like, in an organic solvent such as diethyl ether, THF, or glyme, and the like, at a temperature in range of from about 25° C. to about 100° C., preferably at a temperature in the range of from about 25° C. to about 70° C., to yield the corresponding compound of formula (XI).

The compound of formula (XI), is reacted with a suitably substituted compound (XII) wherein $R^{10}$, $R^{11}$ and the carbon atom of the —C(O)— group to which they are bound are taken together represent $R^3$ in the desired compound of formula (I) (for example, wherein $R^3$ is cyclohexyl, the compound of formula (XII) is cyclohexone), a known compound or compound prepared by known methods, in the presence of reducing agent, such as sodium triacetoxyborohydride, and the like, in an organic solvent, such as dichloromethane, dichloroethane, THF, and the like, or a reducing agent such as sodium borohydride in a protic solvent such as methanol or ethanol, and the like, or a reducing agent such as sodium cyanoborohydride, with a catalytic amount of an acid, such as acetic acid, HCl, or the like, in an organic solvent, such as methanol, acetonitrile, and the like, to yield the corresponding compound of formula (XIII).

The compound of formula (XIII) is reacted with a suitably substituted compound of formula (XIV), wherein $Pg^2$ is a suitable nitrogen protecting group such as Boc, Cbz, and the like, preferably Boc, a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (XV).

The compound of formula (XV), wherein $Pg^1$ is benzyl is reacted with hydrogen gas, at a pressure in the range of from about atmospheric pressure to about 100 psi, preferably at a pressure in the range of from about 30 psi to about 60 psi, in the presence of a catalyst, such as palladium on carbon, palladium hydroxide, and the like, in a protic solvent, such as ethanol, methanol, and the like, to yield the corresponding compound of formula (XVI).

The compound of formula (XVI) is reacted with a suitably substituted compound of formula (XVII), wherein J is fluoro or chloro, a known compound or compound prepared by known methods, in the presence of a base such as $K_2CO_3$, $CsCO_3$, and the like, in an organic solvent such as DMF, DMA, and the like, preferably DMF, at an elevated temperature in the range of from about 25° C. to about 150° C., preferably, at an elevated temperature in the range of from about 100° C. to about 120° C., optionally in the presence of microwave irradiation, to yield the corresponding compound of formula (XVIII).

The compound of formula (XVIII) is de-protected according to known methods to yield the corresponding compound of formula (XIX). For example, wherein the compound of formula (XVIII), $Pg^2$ is Boc, the compound of formula (XVIII) is reacted with an acid, such as trifluoroacetic acid, formic acid, and the like, in an organic solvent such as dichloromethane, chloroform, and the like, to yield the corresponding compound of formula (XIX).

The compound of formula (XIX), is reacted with a reducing agent, such as sodium triacetoxyborohydride, optionally in the presence of a dehydrating agent, such as molecular sieves, sodium sulfate, magnesium sulfate, and the like, in an organic solvent, such as dichloromethane, dichloroethane, THF, and the like, or a reducing agent such as sodium borohydride in a protic solvent such as methanol, ethanol, and the like, or a reducing agent such as sodium cyanoborohydride, with a catalytic amount of an acid, such as acetic acid, HCl, and the like, in an organic solvent, such as methanol, acetonitrile, and the like, to yield the corresponding compound of formula (XX).

The compound of formula (XX) is reacted with hydrogen gas, in the presence of a catalyst such as Pd on carbon (Pd/C), and the like, in a protic solvent such as methanol, ethanol, and the like, to yield the corresponding compound of formula (XXI). Alternatively, the compound of formula (XX) is reacted with a reducing agent such as stannous chloride, and the like, in an organic solvent such as methanol, ethanol, ethyl acetate, THF and the like, or in an acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, optionally in the presence of microwave irradiation, to yield the corresponding compound of formula (XXI).

The compound of formula (XXI) is reacted with cyanogen bromide, and the like, in an organic solvent such as methanol, ethanol, toluene, and the like, to yield the corresponding compound of formula (Ia). Alternatively, the compound of formula (XIII) is reacted with 2-methyl-2-thiopseudourea, in the presence of an acid such as hydrochloric acid, sulfuric acid, and the like, in an organic solvent such as butanol, and the like, to yield the corresponding compound of formula (Ia).

Compounds of formula (I) wherein Y is —N($R^3$)— may be prepared according to the process outlined in Scheme 2 below.

Scheme 2

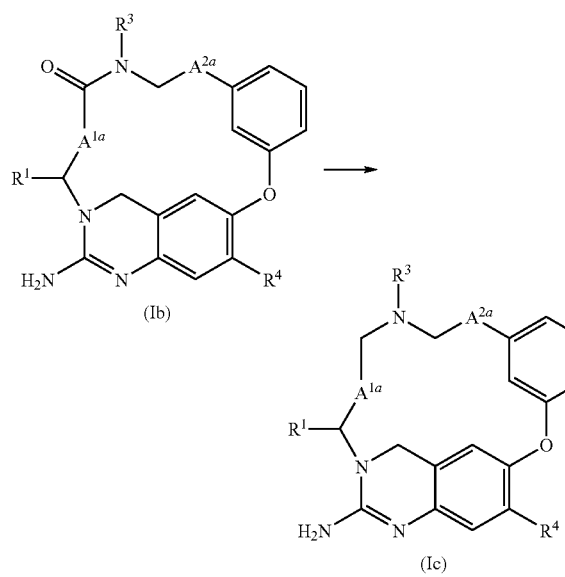

Accordingly, a suitably substituted compound of formula (Ib), wherein $A^{2a}$ is as defined in Scheme 1 above and wherein $A^{1a}$ represents the desired $A^1$ spacer absent a —CH$_2$— group on the portion of the $A^1$ group bound to the Y group (for example, wherein $A^1$ in the desired compound of formula (I) is —CH$_2$—CH$_2$—CH$_2$—, then $A^{1a}$ is —CH$_2$—CH$_2$—; wherein $A^1$ in the desired compound of formula (I) is —CH$_2$—CH$_2$—O—, then $A^{1a}$ is —CH$_2$—O—; and so forth), is reacted with a reducing agent such as borane-tetrahydrofuran, lithium aluminum hydride, and the like, in an organic solvent such as diethyl ether, THF, or glyme, and the like, at a temperature in the range of from about 25° C. to about 100° C., preferably at a temperature in the range of from about 25° C. to about 70° C., to yield the corresponding compound of formula (Ic).

Compounds of formula (I) wherein X is —N—, Q is —CH=, Y is —N(R$^3$)—C(O)—, R$^2$ is 1,3-phenyl and Z is —O— may be prepared according to the process outlined in Scheme 3 below.

Scheme 3

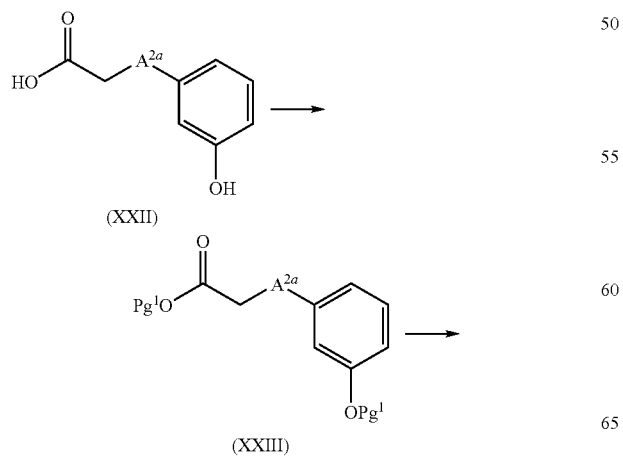

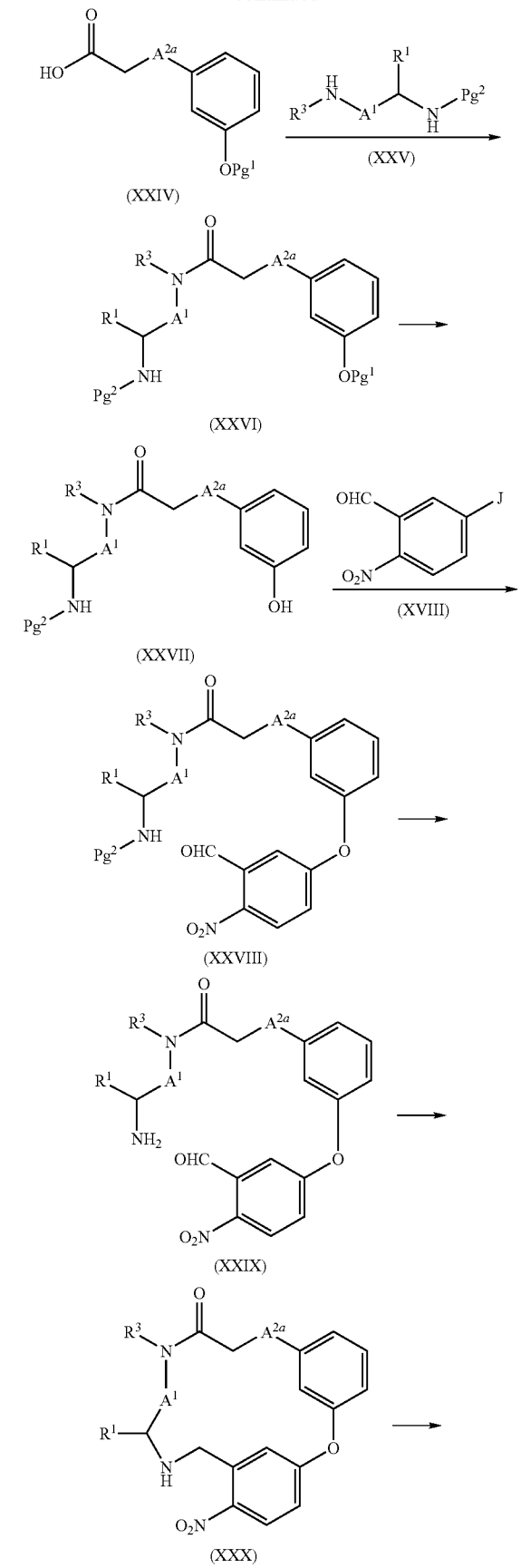

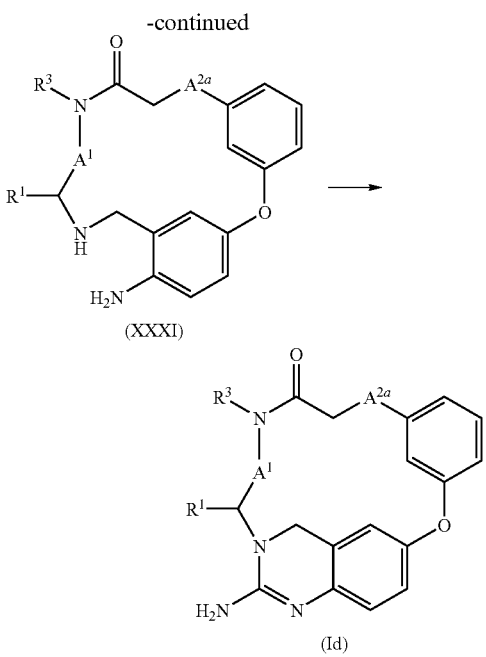

Accordingly, a suitably substituted compound of formula (XXII), wherein $A^{2a}$ represents the desired $A^2$ spacer absent a —$CH_2$— group on the portion of the $A^2$ group bound to the Y group (for example, wherein $A^2$ in the desired compound of formula (I) is —$CH_2$—$CH_2$—$CH_2$—, then $A^{2a}$ is —$CH_2$—$CH_2$—; wherein $A^2$ in the desired compound of formula (I) is —$CH_2$—CH=CH—, then $A^{2a}$ is —CH=CH—; and so forth) a known compound or compound prepared by known methods, is protected according to known methods, to yield the corresponding compound of formula (XXIII), wherein $Pg^1$ is the corresponding protecting group. For example, wherein $Pg^1$ is benzyl, the compound of formula (XXIII) is reacted with a benzyl halide, such as benzyl bromide, benzyl chloride, and the like, in the presence of a base, such as potassium carbonate, or sodium hydroxide, and the like, optionally in the presence of an iodide, such as sodium iodide or potassium iodide, and the like, in an organic solvent such as acetone, DMF, and the like, at a temperature in the range of from about 25° C. to about 120° C., preferably at a temperature in the range of from about 50° C. to about 80° C., to yield the corresponding compound of formula (XXIII).

The compound of formula (XXIII), is reacted with a base, such as sodium hydroxide or potassium hydroxide, and the like, in an organic solvent, such as acetone, dioxane, and the like, optionally in a mixture with a protic solvent such as water, methanol, and the like, to yield the corresponding compound of formula (XXIV).

The compound of formula (XXIV) is reacted with a suitably substituted compound of formula (XXV), wherein $Pg^2$ is a suitable nitrogen protecting group such as Boc, Cbz, and the like, preferably Boc, a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (XXVI).

The compound of formula (XXVI) wherein $Pg^1$ is benzyl, is reacted with hydrogen gas, at a pressure in the range of from about atmospheric pressure to about 100 psi, preferably at a pressure in the range of from about 30 psi to about 60 psi, in the presence of a catalyst, such as palladium on carbon, palladium hydroxide, and the like, in a protic solvent, such as ethanol, methanol, and the like, to yield the corresponding compound of formula (XXVII).

The compound of formula (XXVII) is reacted with a suitably substituted compound of formula (XVII), wherein J is fluoro or chloro, a known compound or compound prepared by known methods, in the presence of a base such as $K_2CO_3$, $CsCO_3$, and the like, in an organic solvent such as DMF, DMA, and the like, preferably DMF, at an elevated temperature in the range of from about 25° C. to about 150° C., preferably, at an elevated temperature in the range of from about 100° C. to about 120° C., optionally in the presence of microwave irradiation, to yield the corresponding compound of formula (XXVIII).

The compound of formula (XXVIII) is de-protected according to known methods to yield the corresponding compound of formula (XXIX). For example, wherein the compound of formula (XXVIII), $Pg^2$ is Boc, the compound of formula (XVIII) is reacted with an acid, such as trifluoroacetic acid, formic acid, and the like, in an organic solvent such as dichloromethane, chloroform, and the like, to yield the corresponding compound of formula (XXIX).

The compound of formula (XXIX), is reacted with a reducing agent, such as sodium triacetoxyborohydride, optionally with a dehydrating agent, such as molecular sieves, sodium sulfate, magnesium sulfate, and the like, in an organic solvent, such as dichloromethane, dichloroethane, THF, or the like, or with a reducing agent such as sodium borohydride in a protic solvent such as methanol, ethanol, and the like, or with a reducing agent such as sodium cyanoborohydride, with a catalytic amount of an acid, such as acetic acid, HCl, and the like, in an organic solvent, such as methanol, acetonitrile, and the like, to yield the corresponding compound of formula (XXX).

The compound of formula (XXX) is reacted with hydrogen gas, in the presence of a catalyst such as Pd on carbon (Pd/C), and the like, in a protic solvent such as methanol, ethanol, and the like, to yield the corresponding compound of formula (XXXI). Alternatively, the compound of formula (XXX) is reacted with a reducing agent such as stannous chloride, and the like, in an organic solvent such as methanol, ethanol, ethyl acetate, THF and the like, or in acid such as concentrated HCl, and the like; or with a reducing agent such as zinc, in the presence of an acid source such as ammonium chloride, calcium chloride, HBr, and the like, in an organic solvent such as methanol, ethanol, ethyl acetate, and the like, or in a mixture of an organic solvent and water as a co-solvent, or in aqueous acid such as acetic acid, and the like, optionally in the presence of microwave irradiation, to yield the corresponding compound of formula (XXXI).

The compound of formula (XXXI) is reacted with cyanogen bromide, and the like, in an organic solvent such as methanol, ethanol, toluene, and the like, to yield the corresponding compound of formula (Id). Alternatively, the compound of formula (XXXI) is reacted with 2-methyl-2-thiopseudourea, in the presence of an acid such as hydrochloric acid, sulfuric acid, and the like, in an organic solvent such as butanol, and the like, to yield the corresponding compound of formula (Id).

Compounds of formula (I) wherein —$R^2$-Z- is other than 1,3-phenyl-O—may be similarly prepared according to the processes outlined in Schemes 1-3 above by substituting a suitably selected starting materials and/or reagents, for example by substituting a suitably substituted reagent for the compound of formula (XIII) in Scheme 1 above or for the compound of formula (XXIV) in Scheme 3.

Compounds of formula (I) wherein X is =C— or —C—, Q is —C(R$^4$)=, Y is —C(O)—N(R$^3$)—, R$^2$ is 1,3-phenyl and Z is —O— may be prepared according to the process outlined inn Scheme 4 below.
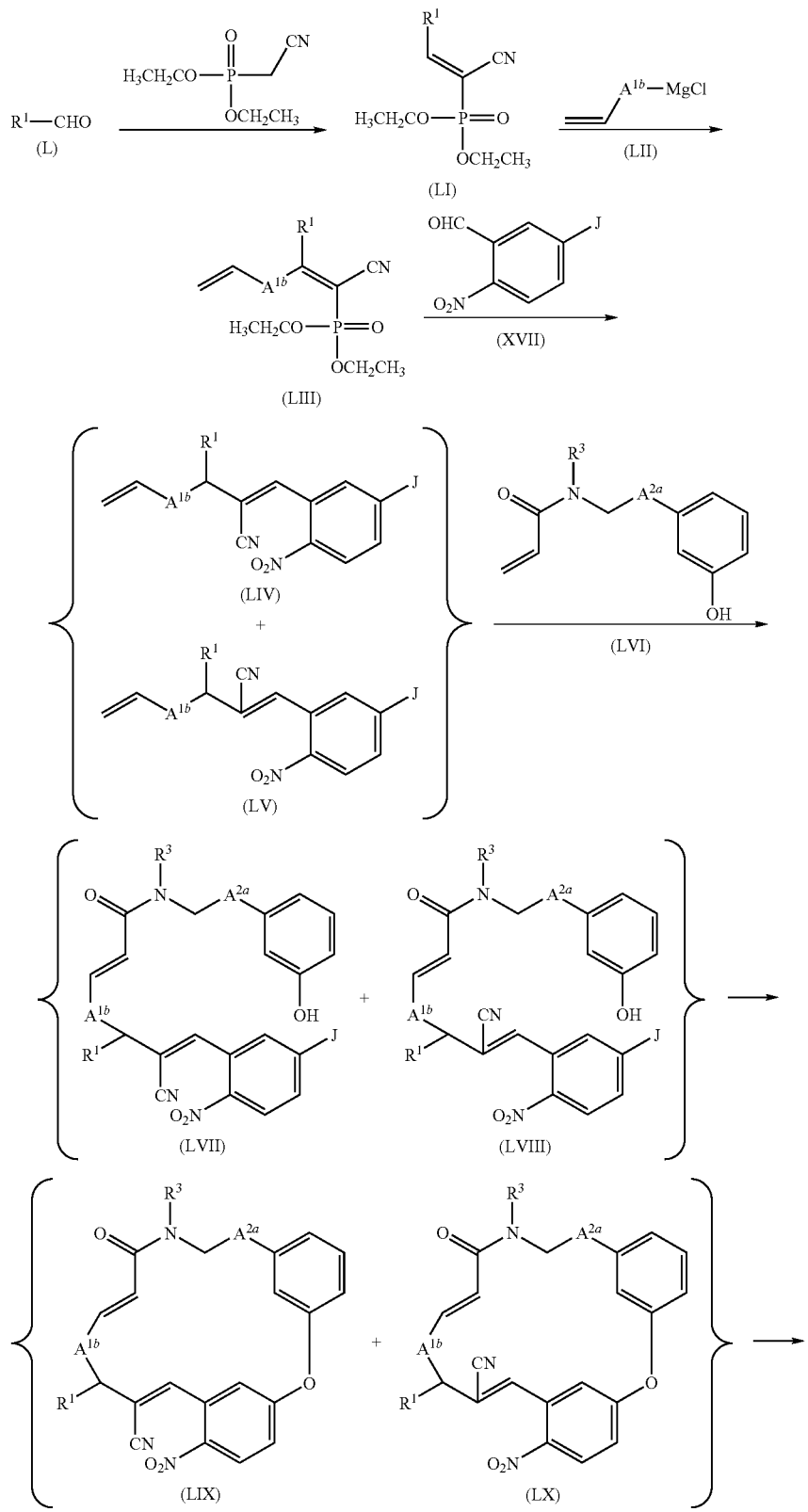

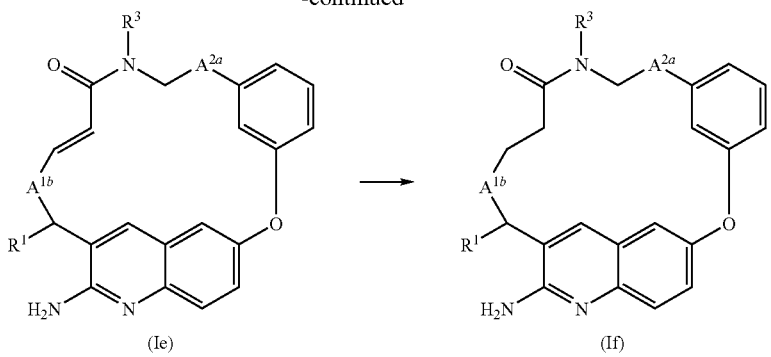

(Ie) → (If)

Accordingly, a suitably substituted compound of formula (L), a known compound or compound prepared by known methods, is reacted with cyanomethyl-phosphonic acid diethyl ester, a known compound, in the presence of an organic amine such as NH$_4$OAc, piperidine, pyridine, and the like, in the presence of an acid such as acetic acid, formic acid, β-alanine, and the like, in an organic solvent such as toluene, ethanol, methanol, and the like, to yield the corresponding compound of formula (LI).

The compound of formula (LI) is reacted with a suitably substituted compound of formula (LII), wherein $A^{1b}$ represents the desired $A^1$ spacer absent a —CH$_2$—CH$_2$— or —CH=CH— group on the portion of the $A^1$ group bound to the Y group (for example, wherein $A^1$ in the desired compound of formula (I) is —CH$_2$—CH$_2$—CH$_2$—, then $A^{1b}$ is —CH$_2$—; wherein $A^1$ in the desired compound of formula (I) is —CH=CH—CH$_2$—, then $A^{1b}$ is —CH$_2$—; and so forth), a known compound or compound prepared by known methods, in the presence of a catalyst such as CuI, CuBr, and the like, in an organic solvent such as THF, diethyl ether, and the like, to yield the corresponding compound of formula (LIII).

The compound of formula (LIII) is reacted with a suitably substituted compound of formula (XVII), wherein J is fluoro or chloro, a known compound or compound prepared by known methods, in the presence of a base such as LHMDS, lithium diisopropylamine, sodium hydride, and the like, in an organic solvent such as THF, diethyl ether, and the like, to yield a mixture of the corresponding compounds of formula (LIV) and (LV), the corresponding (Z) and (E) isomers.

The mixture of the compounds of formula (LIV) and (LV) is reacted with a suitably substituted compound of formula (LVI), $A^{2a}$ represents the desired $A^2$ spacer absent a —CH$_2$— group on the portion of the $A^2$ group bound to the Y group (for example, wherein $A^2$ in the desired compound of formula (I) is —CH$_2$—CH$_2$—CH$_2$—, then $A^{2a}$ is —CH$_2$—CH$_2$—; wherein $A^2$ in the desired compound of formula (I) is —CH$_2$—CH=CH—, then $A^{2a}$ is —CH=CH—; and so forth), a known compound or compound prepared by known methods, in the presence of a olefin metathesis catalyst, such as benzylidenebis(tricyclohexylphosphine)dichlororuthenium (Grubbs first generation catalyst), benzylidene(1,3-dimesitylimidazolidin-2-ylidene)(tricyclohexylphosphine)ruthenium dichloride (Grubbs second generation catalyst), dichloro[[2-(1-methylethoxy-α-O)phenyl]methylene-α-C] (tricyclohexylphosphine)ruthenium (Hoyveda-Grubbs first generation catalyst), [1,3-bis(2,4,6-trimethylphenyl)-2-imidazolidinylidene]dichloro(o-isopropoxyphenylmethylene)ruthenium; (Hoyveda-Grubbs second generation catalyst), or bis[1,1-di(trifluoromethyl)ethoxy][(2,6-diisopropylphenyl)imino](2-methyl-2-phenylpropylidene)molybdenum (Schrock's molybdenum catalyst), and the like, in an organic solvent, such as benzene, toluene, dichloromethane, and the like, at a temperature in the range of from about 25° C. to about 100° C., preferably at a temperature in the range of from about 35° C. to about 75° C., to yield a mixture of the corresponding compounds of formula (LVII) and (LVIII).

The mixture of the compounds of formula (LVII) and (LVIII) is reacted with a base such as K$_2$CO$_3$, CsCO$_3$, and the like, in an organic solvent such as DMF, DMA, and the like, preferably DMF, at an elevated temperature in the range of from about 25° C. to about 150° C., preferably, at an elevated temperature in the range of from about 100° C. to about 120° C., optionally in the presence of microwave irradiation, to yield a mixture of the corresponding compounds of formula (LIX) and (LX).

The mixture of the compounds of formula (LIX) and (LX) is reacted with a reducing agent such as zinc with an acid additive such as ammonium chloride or calcium chloride, in an organic solvent such as methanol, ethanol, and the like, or a with a reducing agent such as stannous chloride, or with a reducing agent such as iron in an acidic solvent such as aqueous HCl, acetic acid, and the like, at a temperature in the range of from about 60° C. to about 150° C., preferably at a temperature in the range of from about 75° C. to about 100° C., to yield the corresponding compound of formula (Ie).

The compound of formula (Ie) is further optionally reacted with hydrogen gas, at a pressure in the range of from about atmospheric pressure to about 100 psi, preferably at atmospheric pressure of about 20 psi, in the presence of a catalyst, such as palladium on carbon, and the like, in a protic solvent, such as ethanol, methanol, and the like, to yield the corresponding compound of formula (If).

Compounds of formula (I) wherein X is —N— and Q is —N= (where Y is —N(R$^3$)—, —N(R$^3$)—C(O)— or —C(O)—N(R$^3$)— and all other variables can as herein defined) may be prepared according to the procedures as described in Example 5 which follows herein. Alternatively, compounds of formula (I) wherein X is —N— and Q is —N= may be prepared as described in the Schemes above, selecting and substituting suitably substituted pyridine acetal (i.e. pyridine aldehyde reagents where the aldehyde is protected).

One skilled in the art will recognize that compounds of formula (I) wherein Q is —C(R$^4$)= and wherein R$^4$ is other than hydrogen may be similarly prepared according to the process outlined in Schemes 1, 3 and 4 above, by selected and substituting a suitably substituted compound of formula (LXX)

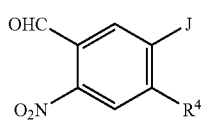

(LXX)

for the compound of formula (XVII). One skilled in the art will further recognize that similar substitution on an R⁴ substituted compound of formula (I) for the compound of formula (Ib) in Scheme 2 will yield the corresponding R⁴ substituted compound for the compound of formula (Ic).

One skilled in the art will further recognize that compounds of formula (I) wherein Y is —NH—C(O)— (i.e. wherein $R^3$ is hydrogen) may be similarly prepared according to the process outlined in Scheme 1, 3 and 4 above.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.1-1000 mg/kg/day, preferably, at a dosage of from about 0.5 to about 500 mg/kg/day, more preferably, at a dosage of from about 0.5 to about 250 mg/kg/day, more preferably, at a dosage of from about 0.5 to about 100 mg/kg/day, more preferably, at a dosage of from about 1.0 to about 50 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, preferably, from about 0.1 to about 500 mg, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by BACE described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, one or more of the compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of disorders mediated by BACE is required.

The daily dosage of the products may be varied over a wide range from 0.01 to 10,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1-1000 mg/kg/day, preferably, at a dosage of from about 0.5 to about 500 mg/kg/day, more preferably, at a dosage of from about 0.5 to about 250 mg/kg/day, more preferably, at a dosage of from about 0.5 to about 100 mg/kg/day, more preferably, at a dosage of from about 1.0 to about 50 mg/kg/day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

Compound #1

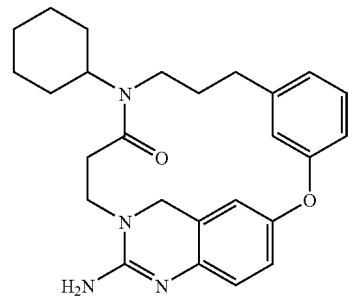

Step A:

A solution of 3-(3-hydroxyphenyl)propionic acid (6.70 g, 40.3 mmol), benzyl bromide (12 ml, 101 mmol), and potassium carbonate (16.7 g, 121 mmol) in acetonitrile (100 mL) was refluxed overnight. After cooling to room temperature, diethyl ether (100 mL) was added to the reaction mixture. The solid in the solution was removed by filtration. The filtrate was concentrated to a residue.

The residue was dissolved in THF (40 mL) and methanol (40 mL). Sodium hydroxide solution (1.0 N, 60 mL, 60 mmol) was added. The resulting solution was stirred at room temperature for 3 hours. The organic solvent was evaporated, and the aqueous phase was extracted with diethyl ether twice. Addition of hydrochloric acid (2.0 N) formed a precipitate which was collected as a white solid.

MH$^-$=255.0

Step B:

To a stirred solution of the solid isolated in Step A (6.04 g, 23.6 mmol) in dichloromethane (100 mL) was added oxalyl chloride (3.0 mL, 35.4 mmol). One drop of DMF was then added. The resulting solution was stirred at room temperature for 4 h and then concentrated to a residue. The residue was dissolved in dichloromethane (100 mL). Cyclohexylamine (3.2 mL, 28.0 mmol) was then added followed by addition of triethylamine (6.4 mL, 46.8 mmol). The resulting solution was stirred at room temperature for one hour. The solution was then extracted with hydrochloric acid (2.0 N) twice and dried over magnesium sulfate. The resulting solution was filtered and concentrated to yield a white solid.

$MH^+$=338.1

Step C:

To a stirred solution of the solid isolated in Step B (7.5 g, 22.2 mmol) in THF (100 mL), lithium aluminum hydride (26.7 mL, 1.0 M in THF, 26.0 mmol) was added slowly. The resulting solution was refluxed 24 hr. The reaction was then quenched by adding methanol. The resulting solution was concentrated to a residue. Hydrochloric acid (6.0 N) was added resulting in the formation of a precipitate. The HCl salt (precipitate) was isolated by filtration to yield a white solid.

$MH^+$=324.1

Step D:

The solid isolated in Step C (2.31 g, 8.89 mmol), N-Boc-β-alanine (1.46 g, 7.72 mmol), N-methylmorpholine (2.7 mL, 26.6 mmol) and HBTU (3.16 g, 8.3 mmol) in DMF (50 mL) were stirred at room temperature overnight. Water (50 mL) was then added to the reaction mixture. The resulting solution was extracted with diethyl ether three times. The combined organic extracts were washed with sodium hydroxide solution (1.0 N) once, hydrochloric acid (1 N) once, and water once, and then dried over magnesium sulfate. The solution was filtered and concentrated to yield a colorless oil.

$MH^+$=495.3

Step E:

A mixture of the oil isolated in Step D (3.72 g, 7.5 mmol) and 10% Pd on carbon (2.0 g) in ethanol (150 mL) was hydrogenated at 50 psi at room temperature overnight. The resulting solution was filtered and concentrated to a residue. The residue was dissolved in diethyl ether (150 mL). The resulting solution washed with water and dried over magnesium sulfate. The solution was filtered and concentrated to yield a colorless oil.

$MH^+$=405.2

Step F:

A solution of the oil isolated in Step E (2.80 g, 6.92 mmol), 5-fluoro-2-nitrobenzaldehyde (1.17 g, 6.92 mmol), potassium carbonate (1.43 g, 10.3 mmol) in DMF (50 ml) was stirred at 50° C. overnight. Water (50 mL) was then added to the reaction mixture. The resulting solution was extracted with diethyl ether twice. The combined organic solution washed with water twice, dried over magnesium sulfate. The solution was filtered and concentrated to a residue. The residue was purified over silica gel column eluted with heptane/ethyl acetate (1:1) to yield a as white solid.

$MH^+$=554.8.

Step G:

The solid isolated in Step F (2.61 g, 4.71 mmol) was dissolved in TFA (20 mL) and dichloromethane (20 mL) and then stirred at room temperature for 2 hours. The resulting solution was concentrated to a residue, and the residue was dissolved in ethyl acetate. The resulting solution washed with sodium hydroxide (1.0 N) once and water once and then was dried over magnesium sulfate. The solution was concentrated to yield a purple solid.

$MH^+$=454.1

Step H:

To a solution of the solid isolated in Step G (1.00 g, 2.2 mmol) in dichloromethane (90 mL), molecular sieves (4 Å, 12 g) were added. The resulting solution was stirred at room temperature for 3 h, and then $NaBH(OAc)_3$ (0.93 g, 4.4 mmol) was added. The resulting solution was stirred for another 24 h, and then methanol (10 mL) was added. The resulting mixture was filtered through a pad of silica gel and then concentrated to a residue. The residue was purified by Gilson HPLC to yield a white solid.

$MH^+$=438.4

Step I:

To a solution of the solid isolated in Step H (1.14 g, 2.6 mmol) in ethanol (50 mL), tin chloride (2.74 g, 12.1 mmol) was added. The resulting solution was stirred at room temperature overnight. The solution was then concentrated to a residue. The residue was treated with hydrochloric acid (6 N). The white precipitate that formed was collected by filtration. The white solid was dissolved in methanol. The resulting solution was made basic by adding sodium hydroxide solution (1.0 N). The solution was then extracted with diethyl ether three times. The combined diethyl ether extracts were washed with water twice and dried over magnesium sulfate. The solution was filtered and concentrated to a residue.

Step J:

The residue isolated in Step I was dissolved in dichloromethane (30 mL), and cyanogen bromide (3.0 M in dichloromethane, 0.40 mL, 1.2 mmol) was added. The resulting solution was stirred at room temperature for 24 h. The reaction mixture was concentrated to yield a residue which was purified by Gilson HPLC to yield the title compound a white solid, as its corresponding TFA salt.

$MH^+$=433.3

$^1H$ NMR (300 MHz, $CDCl_3$), δ6.78-7.26 (m, 7H), 4.17-4.38 (m, 2H), 3.79-3.97 (m, 3H), 2.20-2.80 (m, 8H), 1.00-2.00 (m, 10H).

EXAMPLE 2

Compound #2

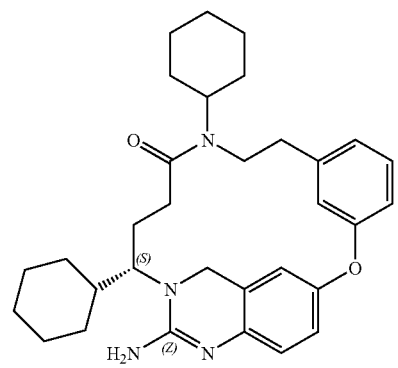

Step A:

To a stirred solution of 3-benzyloxyphenylacetonitrile (24.88 g, 111 mol) in THF (100 mL), a borane-THF (1.0 M, 167 mL, 167 mmol) in THF solution was added. The resulting solution was refluxed overnight. Methanol was then added to destroy excess borane, and the reaction mixture was concentrated. Hydrochloric acid (6 N, 30 mL) was added. The resulting white precipitate from the solution was collected by filtration and dried to yield a solid, as its corresponding HCl salt. The HCl salt was converted to the free base by dissolution in dichloromethane and subsequently washed with sodium hydroxide solution (1.0 N) to yield a colorless oil.
MH$^+$=228.2

Step B:
To a stirred solution of the oil isolated in Step A (5.73 g, 25.2 mmol), cyclohexanone (3.1 ml, 30.2 mmol), acetic acid (5.0 mL) in THF (70 mL) and sodium triacetoxyborohydride (6.41 g, 30.2 mmol) were added. The resulting solution was stirred at room temperature overnight. Diethyl ether (100 mL) was then added, and the solution was filtered. The organic solution washed with sodium hydroxide solution (1.0 N) three times and water once, and then dried over magnesium sulfate. The solution was filtered and concentrated to a residue. The residue was treated with hydrochloric acid (6 N) to yield a white solid, as its corresponding HCl salt.
MH$^+$=310.2

Step C:
A solution of the solid isolated in Step B (2.80 g, 8.1 mmol), 4-tert-butoxycarbonylamino-4-cyclohexyl-butyric acid (2.31 g, 8.1 mmol), N,N-diisopropylethylamine (7.0 ml, 40.2 mmol) and HBTU (3.99 g, 10.5 mmol) in DMF (60 mL) was stirred at room temperature overnight. Water (100 mL) was then added to the reaction mixture. The resulting solution was extracted with diethyl ether three times. The combined organic extracts were washed with sodium hydroxide solution (1.0 N) once, hydrochloric acid (1.0 N) twice, and water once, then dried over magnesium sulfate. The resulting solution was filtered and concentrated to yield a black oil.
MH$^+$=577.4

Step D:
A solution of the oil isolated in Step C (5.0 g, 8.67 mmol), 10% palladium on carbon (3.0 g) in ethanol (150 mL) was hydrogenated at 50 psi at room temperature for 6 hours. The resulting solution was filtered and concentrated to yield a white solid.
MH$^+$=487.5

Step E:
A solution of the white solid isolated in Step D (3.90 g, 8.0 mmol), 5-fluoro-2-nitrobenzaldehyde (1.36 g, 8.0 mmol), and potassium carbonate (1.66 g, 12.0 mmol) in DMF (20 mL) was stirred at 50° C. overnight. Water then was added to the reaction mixture. The resulting solution was extracted with ethyl acetate twice. The combined organic extracts were washed with sodium hydroxide solution (1.0 N) once, hydrochloric acid (1.0 N) twice, and water once, and then dried over magnesium sulfate. The resulting solution was filtered and concentrated to yield a lightly colored oil.
$^1$H NMR (300 MHz, DMSO) δ10.44 (s, 1H), 8.17 (d, J=2 Hz, 1H), 7.36 (m, 2H), 7.20 (m, 2H), 7.01 (s, 1H), 6.94 (m, 1H), 4.50 (m, 1H), 3.56 (m, 1H), 3.40 (m, 2H), 2.85 (m, 2H), 2.40 (m, 2H), 0.80-1.90 (m, 32H)

Step F:
To a stirred solution of the oil isolated in Step E (4.93 g, 7.7 mmol) in dichloromethane (50 mL), TFA (50 mL) was added. The reaction mixture was then stirred at room temperature for 4 hours. The resulting solution was concentrated to a residue. The residue was dissolved in ethyl acetate. The resulting solution washed with sodium hydroxide solution (1.0 N) twice and water one time, and then dried over magnesium sulfate. The resulting solution was filtered and concentrated to yield a yellow solid.
MH$^+$=536.4

Step G:
To a stirred solution of the solid isolated in Step F (5.40 g, 10.1 mmol) in dichloromethane (800 mL), molecular sieves (4 Å, 54 g) were added. The resulting mixture was stirred at room temperature for 30 min. Sodium triacetoxyborohydride (4.27 g, 20.1 mmol) was added. The resulting solution was stirred at room temperature overnight. Then, the reaction mixture was filtered and concentrated to yield a residue which was purified on a silica gel column eluted with ethyl acetate:heptane:triethyl amine in a ratio of 15:84:1 to yield a white solid.
MH$^+$=520.4

Step H:
A mixture of the solid isolated in Step G (1.60 g, 3.1 mmol), 10% palladium on carbon (1.6 g) in a mixture of THF (30 mL) and ethanol (40 mL) was hydrogenated at 50 psi at room temperature for 6 h. The resulting solution was filtered and concentrated to yield a residue.

Step I:
The residue isolated in Step H was dissolved in ethanol (60 mL). Cyanogen bromide (5.0 M in acetonitrile, 0.98 mL, 4.9 mmol) was added, and the reaction mixture was refluxed overnight. After cooling, the resulting solution was concentrated in vacuo to yield a residue which was purified by Gilson HPLC to yield the title compound as a white solid. The white solid was treated with HCl in diethyl ether to yield the title compound as a white solid, as its corresponding HCl salt.
MH$^+$=515.1
$^1$H NMR (300 MHz, DMSO), δ8.17(br s, 2H), 6.87-7.35 (m, 7H), 4.75 (d, J=15 Hz, 1H), 4.10 (d, J=15 Hz, 1H), 3.65 (m, 1H), 3.52 (m, 1H), 3.05 (m, 1H), 2.80 (m, 2H), 2.70 (m, 1H), 2.00 (m, 1H), 0.60-1.90 (m, 23H)

EXAMPLE 3

4-tert-Butoxycarbonylamino-4S-cyclohexyl-butyric acid

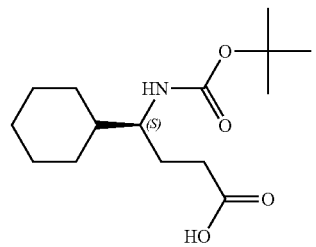

Step A
To an ice cooled solution of Boc-D-cyclohexylglycine (10 g, 39 mmol), N,O-dimethylhydroxyamine HCl salt (4.6 g, 46 mmol) and HOBT (7 g, 51 mmol) in CH$_2$Cl$_2$ (200 mL), TEA (11 mL) was added followed by addition of EDC (10 g, 51 mmol). The reaction mixture was allowed to warm to room temperature and was then stirred overnight. EtOAc (300 mL) was added. The reaction mixture was then washed with citric acid solution, NaHCO$_3$ solution, and NaCl solution. The organic layer was collected, dried with MgSO$_4$ and evaporated to yield a colorless oil. The colorless oil was used in subsequent reactions without further purification.
MH+301.2

Step B

To an ice cooled solution of the colorless oil isolated in Step A above (12.3 g, 40 mmol) in THF (100 mL) was slowly added LAH (1M solution in THF, 45 mL), keeping the reaction temperature below about 5° C. The ice bath was removed, and the reaction mixture was stirred at room temperature for 20 min. A solution of NaHSO$_4$ (7.3 g) in water (10 mL) was slowly added to quench the reaction. The reaction mixture was then filtered through Celite®. EtOAc (300 mL) was added to the filtrate, and the organic layer washed with NaCl solution, dried with MgSO$_4$ and evaporated to yield an oil. The oil was used in subsequent reactions without further purification.

MH+242.2

Step C

To an ice cooled solution of trimethyl phosphonoacetate (19 mL, 0.11 mol) in THF (200 mL) was added 60% NaH (3.1 g, 0.08 mol) in portions. The ice bath was removed, and the reaction mixture was stirred at room temperature for 30 min. The reaction mixture was cooled to 0° C., then a solution of the oil isolated in Step B (9 g, 37 mmol) in THF (200 mL) was added. The reaction mixture was stirred at room temperature for another 20 min. Water (100 mL) was added, and most of the THF was evaporated. The product was extracted into EtOAc (400 mL), and the organic layer washed with NaCl solution and dried with MgSO$_4$. Column chromatography (1:1 heptane:EtOAc) yielded a white solid.

1H NMR (300 MHz, CDCl3): δ1.1-1.3 (m, 7H), 1.44 (s, 9H), 1.6-1.8 (m, 5H), 3.73 (s, 3H), 4.17 (m, 0.6×1H), 4.58 (m, 0.4×1H), 5.9 (dd, J=1.4 Hz, J=15.6 Hz, 1H), 6.88 (dd, J=5.6 Hz, J=15.6 Hz, 1H).

Step D

To a solution of the white solid isolated in Step C (9 g, 30 mmol) in MeOH (100 mL) was added 10% Pd on activated carbon (1 g) under N$_2$. The reaction mixture was hydrogenated at 20 psi for 4 hours. The catalyst was removed by filtration, and the MeOH was evaporated to yield a white solid.

1H NMR (300 MHz, CDCl3): δ0.9-1.3 (m, 7H), 1.43 (s, 9H), 1.5-1.8(m, 6H), 2.37 (t, J=7.52 Hz, 2H), 3.4 (m, 1H), 3.67 (s, 3H), 4.29 (m, 1H).

Step E

To a solution of the solid isolated in Step D (9 g) in MeOH (100 mL) was added 1N NaOH (31 mL). The reaction mixture was stirred at room temperature overnight. Citric acid (7 g) was added, and the MeOH was removed in vacuo. The product was extracted into EtOAc (300 mL). The organic layer washed with NaCl solution and then dried with MgSO$_4$ to yield the title compound as a white solid.

MH−284.1

EXAMPLE 4

4-tert-Butoxycarbonylamino-5-methyl-hexanoic acid

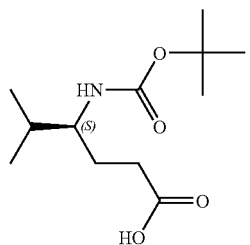

Step A: (R)-[1-(2,2-Dimethyl-4,6-dioxo-[1,3]dioxane-5-carbonyl)-2-methyl-propyl]-carbamic acid, tert-butyl ester A 5 L four-necked flask (equipped with mechanical stirrer, nitrogen inlet, thermocouple, and glass stopper) was charged with Boc-D-Valine (143.6 g, 0.661 mol) and dichloromethane (2.8 L). The reaction was chilled to ~3° C. in an ice bath, and then 4-N,N-dimethylaminopyridine (124.6 g, 1.02 mol) and Meldrum's acid (104.8 g, 0.727 mol) were added to the reaction. To the reaction mixture was then added 1-[3-(dimethylaminopropyl)]-3-ethylcarbodiimide hydrochloride (EDCl, 139.4 g, 0.727 mol) over a five-minute period, and then the reaction mixture was allowed to warm to room temperature over 18 h (overnight). The reaction mixture washed with 5% (w/w) aqueous potassium bisulfate (4×600 mL), dried (MgSO$_4$), and the solution was used directly in the next step without concentration or purification. A small portion was concentrated and displayed the following analytical data.

Mass Spectrum (Electrospray, Negative mode): m/z=342 (M−1).

HPLC: R$_f$=5.051 min; ABZ+PLUS, 3 μm, 2.1×50 mm

Gradient: A=water (0.1% TFA), B=ACN (0.1% TFA) @ 0.75 mL/min Initial: A:B, 90:10.t=0.00-4.00 min (A:B, 10:90), t=4.00-4.10 min (A:B, 0:100), t=4.10-6.00 min (A:B, 0:100)

Step B: (S)-[1-(2,2-Dimethyl-4,6-dioxo-[1,3]dioxan-5-ylmethyl)-2-methyl-propyl]-carbamic acid, tert-butyl ester In a 5 L one-neck flask four-necked flask (equipped with mechanical stirrer, nitrogen inlet, thermocouple, and glass stopper), was charged the solution of (R)-[1-(2,2-dimethyl-4,6-dioxo-[1,3]dioxane-5-carbonyl)-2-methyl-propyl]-carbamic acid, tert-butyl ester in dichloromethane prepared in Step A above, (~3.2 L). The reaction was chilled to ~3° C. in an ice bath, and acetic acid was added (437 g, 7.27 mol). The reaction mixture was then treated with sodium borohydride granules (62.5 g, 1.65 mol), which were added in portions over 1 h. During the addition the reaction temperature increased to ~9° C. and was stirred at that temperature 1.5 h and then was split into two portions. Each portion was poured into brine (1 L), stirred (magnetically) for 20 minutes, and partitioned. Each organic phase washed with brine (3×750 mL) and distilled water (2×500 mL). The combined organic phases were dried (MgSO$_4$) and concentrated to yield crude product. The crude product was dissolved in heptane-dichloromethane (~1:1) and loaded onto a Biotage 150M cartridge (2.5 kg silica gel) and then eluted with heptane (2 L), 15:85 (14 L), 3:7 (16 L), and 1:1 ethyl acetate-heptane (8 L) to give two main fractions. The first fraction yielded the desired material contaminated with minor impurities.

Melting Point: 108-112° C.

Optical Rotation: [α]$_D$=−10.2° (c 4.15, MeOH, 23° C.)

The second fraction yielded additional product, which displayed the following analytical data.

Melting Point: 115-117° C.

Optical Rotation: [α]$_D$=−11.2° (c 4.18, MeOH, 23° C.)

Mass Spectrum (Electrospray, Negative mode): m/z=328 (M−1)

HPLC: R$_f$=3.700 min; ABZ+PLUS, 3 μm, 2.1×50 mm

Gradient: A=water (0.1% TFA), B=ACN (0.1% TFA) @ 0.75 mL/min Initial: A:B, 90:10.t=0.00-4.00 min (A:B, 10:90), t=4.00-4.10 min (A:B, 0:100), t=4.10-6.00 min (A:B, 0:100)

Step C: (S)-2-Isopropyl-5-oxo-pyrrolidine-1-carboxylic acid, tert-butyl ester

In a 3 L, one-necked flask (equipped with a magnetic stir bar and a condenser with nitrogen inlet) was charged (S)-[1-(2,2-dimethyl-4,6-dioxo-[1,3]dioxan-5-ylmethyl)-2-methyl-propyl]-carbamic acid, tert-butyl ester prepared in Step B above (147 g, 0.446 mol) and toluene (1.4 L). The reaction mixture was heated to reflux for 4 h then cooled to room temperature and concentrated in vacuo to yield crude product as a residual oil. The crude product was dissolved in heptane (~200 mL) and loaded onto a Biotage 75 L (800 g silica gel) and eluted with heptanes (1 L), 1:9 (7 L), and 1:3 ethyl acetate-heptane (2 L) to yield the product as an oil.

Optical Rotation: $[\alpha]_D=-71.9°$ (c 1.05, $CHCl_3$, 23° C.); lit value (R)+77.4° (c 1.4, $CHCl_3$)

Optical Rotation: $[\alpha]_D=-72.2°$ (c 0.983, MeOH, 23° C.)

Elemental Analysis: $C_{12}H_{21}NO_3$:
Calculated: % C=63.41, % H=9.31, % N=6.16 Found: % C=63.51, % H=9.35, % N=6.41

Step D: (S)-4-tert-Butoxycarbonylamino-5-methyl-hexanoic acid

A 2 L, one-necked flask (equipped with a magnetic stir bar and a nitrogen inlet) was charged with (S)-2-isopropyl-5-oxo-pyrrolidine-1-carboxylic acid, tert-butyl ester prepared in Step C above (77.4 g, 0.341 mol) and acetone (260 mL). To this solution was added 1M aqueous sodium hydroxide (408 mL, 0.408 mol), and the reaction mixture was stirred 30 minutes. The acetone was removed in vacuo and the resulting aqueous slurry was acidified, with vigorous stirring, by addition of solid sodium bisulfate (55 g, 0.45 mol) and diluted to 1 L with deionized water. The slurry was stirred for 2 h and the resulting white solid was collected by filtration, washed with deionized water, and dried in a vacuum oven to yield the product as a white solid.

Melting Point: 107-109° C.

Optical rotation: $[\alpha]_D=-6.40°$ (c 4.13, MeOH, 23° C.); lit value (R)+2.9° (c 1.4, EtOH)

Mass Spectrum (Electrospray, Positive mode): m/z=267.9 ($M^+Na$)

Elemental Analysis: $C_{12}H_{23}NO_4$:
Calculated: % C=58.75, % H=9.45, % N=5.71
Found: % C=58.84, % H=9.21, % N=5.60

The opposite enantiomer was prepared in an identical fashion starting from Boc-L-Valine and gave the following analytical data.

Melting Point: 91-95° C.

Optical rotation: $[\alpha]_D=+5.49°$ (c 3.16, MeOH, 23° C.)

Mass Spectrum (Electrospray, Positive mode): m/z=268.0 (M+Na)

Karl Fisher Titration: 0.20% (w/w); indicated 0.3 mol eq. hydrate.

Elemental Analysis: $C_{12}H_{23}NO_4 \cdot 0.3H_2O$:
Calculated: % C=57.49, % H=9.49, % N=5.59
Found: % C=57.78, % H=10.04, % N=5.21

EXAMPLE 5

Compound #32

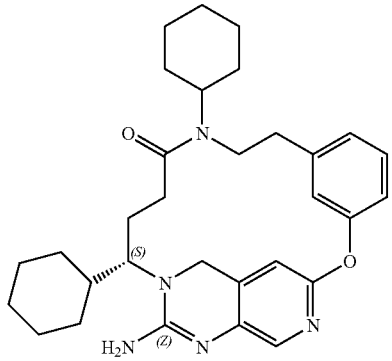

Step A:
2-Chloro-4-methyl-5-nitro-pyridine (8.0 g, 46 mmol) and N,N-dimethyl formamide dimethylacetal (7.6 mL, 57.5 mmol) were added into DMF (50 mL) and heated at 150° C. for four hours. The DMF was removed under reduced pressure, and the crude residue was taken into $THF:H_2O$ (1:1, 200 mL).

Sodium periodate (22.0 g, 102 mmol) was added, and the reaction was stirred at room temperature overnight. Ethyl acetate was added and the solid precipitate was filtered off. The organic layer washed with saturated aqueous $NaHCO_3$ and brine. The solvent was dried over sodium sulfate and removed in vacuo to yield crude material. The crude material was purified on a normal phase column (DCM) to yield a clear oil.

$^1$H NMR (300 MHz, $CDCl_3$) $\delta$ 7.6 (s, 1 H), 9.2 (s, 1 H), 11.4 (s, 1 H).

Step B:
The oil from step A (2.8 g, 15 mmol), p-toluenesulfonic acid (3.14 g, 16.5 mmol), and triethyl orthoformate (3.5 mL, 21 mmol) were taken up into dichloroethane (20 mL) and heated at 50° C. for four hours. The reaction was quenched with water and extracted with ethyl acetate. The organic layer was washed with saturated aqueous $NaHCO_3$ and brine. The solvent was dried over sodium sulfate and removed in vacuo to yield a yellowish oil.

$^1$H NMR (300 MHz, $CDCl_3$) $\delta$ 1.25 (t, 6H), 3.1-3.4 (m, 4 H), 6.05 (s, 1 H), 7.8 (s, 1H), 8.9 (s, 1 H).

Step C:
3-Benzyloxyphenylacetonitrile (10.0 g, 45 mmol) was taken into THF (50 mL), and borane (55.0 mL, 55 mmol, 1N in THF) was added. The reaction was refluxed overnight. The reaction was cooled to room temperature and quenched with saturated aqueous $NaHCO_3$. The aqueous layer was extracted with ethyl acetate and the organic layer washed with brine. The solvent was removed in vacuo to yield a thick, clear oil.

$^1$H NMR (300 MHz, DMSO): $\delta$ 2.8 (t, 2H), 3.0 (t, 2H), 5.05 (s, 2H), 6.8-7.0 (m, 3H), 7.2-7.5 (m, 6H), 7.95 (s, 2H).

Step D:
The oil from step C (6.0 g, 26.5 mmol) and cyclohexanone (3.3 mL, 31.8 mmol) were taken into THF (25 mL), and sodium triacetoxyborohydride (8.4 g, 39.8 mmol) was added. The reaction mixture was stirred overnight at room temperature. The reaction mixture then was filtered and quenched with saturated aqueous $NaHCO_3$ and extracted with ethyl acetate. The organic layer washed with brine, dried over sodium sulfate, and evaporated in vacuo to yield a yellow oil.

$MH^+$310.1

Step E:
The oil from step D (7.0 g, 22.7 mmol) was taken into 25 mL DMF and (S)-4-t-butoxycarbonylamino-4-cyclohexyl-butyric acid (6.45 g, 22.5 mmol) HOBt (3.83 g, 28.4 mmol), EDC (5.45 g, 28.4 mmol) and DIPEA (6.0 mL, 34 mmol). The reaction was stirred at room temperature overnight. The reaction was quenched with water and extracted with ethyl acetate. The organic layer washed with saturated aqueous $NaHCO_3$ and brine, dried over sodium sulfate and purified on a normal phase column with DCM:MeOH (99:1) to yield a light yellow oil.

$MH^+$577.2

Step F:
The oil from step E (6.0 g, 10.4 mmol) was taken into ethanol (40 mL) and 10% Pd/C (1.0 g) was added under argon. The reaction was placed on the hydrogenator and shaken at 40 psi for six hours. The reaction was filtered through Celite®, and the solvent was removed in vacuo to yield a residue.

MH+487.2

Step G:

The crude material from step F (5.1 g, 10 mmol) was taken into DMF (20 mL) and the oil from step B (2.7 g, 10 mmol) was added. Cesium carbonate (4.9 g, 15 mmol) was added and the reaction was stirred at 50° C. for two hours. The reaction was quenched with water and extracted with ethyl acetate. The organic layer washed with saturated aqueous NaHCO$_3$ and brine, dried over sodium sulfate and evaporated in vacuo to yield crude product as a residue. The crude material was purified on a normal phase column (DCM:MeOH) to yield a light yellow solid.

MH+711.5

Step H:

The solid from step G (2.5 g, 3.5 mmol) was taken into DCM (10 mL) and TFA (2.5 mL) was added. The reaction mixture was stirred for five hours at room temperature. The reaction mixture was then diluted with DCM (300 mL) and washed (2×) with saturated aqueous NaHCO$_3$ and brine. The organic layer was dried over sodium sulfate and filtered. Sodium triacetoxyborohydride (1.5 g, 7.0 mmol) was added to the filtrate, and the reaction mixture was stirred at room temperature overnight. The reaction mixture was filtered and washed with saturated aqueous NaHCO$_3$ and brine, dried over sodium sulfate, and the solvent was removed in vacuo to yield crude material. The crude material was purified on a normal phase column (DCM:MeOH) to yield a solid.

MH+521.2

Step I:

The solid from step H (0.30 g, 0.57 mmol) was taken into ethanol (10 mL) and 10% Pd/C (0.25 g) was added under argon. The reaction was placed on the hydrogenator and shaken at 40 psi for four hours. The reaction mixture was filtered through Celite®, and the solvent was removed in vacuo to yield a solid.

MH+491.4

Step J:

The solid from step 1 (0.28 g, 0.57 mmol) was taken into ethanol (10 mL) and cyanogen bromide (0.29 mL, 0.86 mmol, 3M in DCM) was added. The reaction mixture was stirred at 80° C. for four hours. The solvent was removed in vacuo and the crude material was taken up in DCM. The organic layer was washed with saturated aqueous NaHCO$_3$ and brine, dried over sodium sulfate and evaporated in vacuo to yield a residue. The residue was purified on a normal phase column (DCM:MeOH:NH$_3$) to yield a residue. The residue was dissolved in isopropanol, and 1N HCl was added until the mixture was acidic. Water was added, and the mixture was frozen and lyophilized to yield the title compound as a white powder.

MH+516.3

$^1$H NMR (300 MHz, CDCl$_3$): δ1.0-1.95 (m, 23H), 2.05-2.4 (m, 2H), 2.52 (t, 1 H), 2.75-3.0 (m, 2H), 3.25 (m,1 H), 3.7-4.1 (m, 3H), 4.42 (d, 1 H), 6.25 (s, 1 H), 6.38 (s, 1 H), 6.95 (s, 1 H), 7.1 (d, 1 H), 7.25 (t, 1 H), 8.15 (s, 1 H), 8.4 (s, 1 H), 11.2 (s, 1 H).

EXAMPLE 6

Compound #39

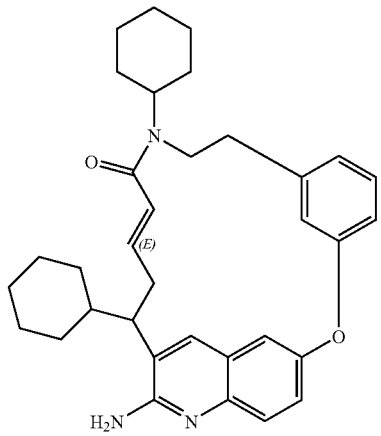

Step A: [1-Cyano-2-(cyclohexanyl)-vinyl]-phosphonic acid diethyl ester

To a stirred solution of diethyl cyanomethylphosphonate (32.6 g, 184 mmol), ammonium acetate (6.0 g, 78 mmol), acetic acid (6 mL) in toluene (120 mL) was added cyclohexanecarboxaldehyde (21 g, 174 mmol). The reaction mixture was stirred at room temperature for two days and then heated at 100° C. for 3 hours. After cooling, the reaction mixture washed with saturated sodium bicarbonate solution three times, with brine one time and then dried over magnesium sulfate. The reaction mixture was filtered and concentrated to yield a residue. The residue was purified by Kugelrohr distillation to yield [1-cyano-2-(cyclohexyl)-vinyl]-phosphonic acid diethyl ester as a light brown oil.

Step B: (1-Cyano-2-cyclohexyl-pent-4-enyl)-phosphonic acid diethyl ester

To a stirred mixture of the oil isolated in Step A (17.5 g, 65 mmol), and cuprous iodide (0.75 g) in THF (100 mL) at 0° C., a solution of allylmagnesium bromide in THF (2 M, 42 mL, 84 mmol) was added slowly while the temperature was maintained at about 5-10° C. The reaction mixture then was stirred at room temperature overnight. Aqueous saturated ammonium chloride solution (100 mL) was then added. The reaction mixture was stirred 30 min at room temperature and then extracted with ethyl acetate (200 mL). The organic solution washed with saturated ammonium chloride solution three times and with brine one time, and then was dried over sodium sulfate. The reaction mixture was then filtered and concentrated to yield a residue. The residue was purified by Kugelrohr distillation to yield a colorless oil (GC showed it contained 20% starting material, but the oil was used as is without further purification).

MH+=314.

Step C: 3-Cyclohexyl-2-(5-fluoro-2-nitro-benzylidene)-hex-5-enenitrile

To the oil isolated in Step B (10 g, 0.021 mmol) in THF (80 mL) at about 5-8° C., LHDMS (1.0 M, 26 mL, 26 mmol) was added slowly. The reaction mixture was stirred for 30 minutes and then a solution of 2-nitro-5-phenoxybenzaldehyde (4 g, 21 mmol) in THF (20 mL) was added. The reaction mixture was stirred at room temperature overnight. Saturated aqueous ammonium chloride solution (80 mL) was added. The reaction mixture was extracted with ethyl acetate three times. The combined organic extracts were washed with brine and dried over sodium sulfate. The reaction mixture was filtered and concentrated to yield a brown residue which was purified by silica gel column chromatography by eluting with ethyl acetate:heptane (1:20) to yield a residue which had the Z-isomer as the major component and the E-isomer as the minor component.

MH+=329

STEP D: [2-(3-Benzyloxy-phenyl)-ethyl]-cyclohexyl-amine

To a stirred solution of the residue (7.66 g, 34 mmol) isolated in Step C and cyclohexanone (3.24 g, 33 mmol) in dichloroethane (150 mL) was added sodium triacetoxyborohydride (10.5 g, 50 mmol). The resulting solution was stirred at room temperature overnight and was then added to ethyl acetate (600 mL). The resulting mixture washed with 1N NaOH solution (2×50 mL), water (2×100 mL), and saturated NaCl solution. The solution was then concentrated to yield an oil.

MH+=310

Step E: 3-(2-Cyclohexylamino-ethyl)-phenol

A stirred solution of the oil isolated in Step D (4.5 g, 14 mmol) and Pd/C (10%, 150 mg) in ethanol (100 mL) was hydrogenated under 1 atm of hydrogen overnight. The catalyst was filtered off, and the solvent was removed in vacuo to yield an oil.

MH+=220

Step F: N-Cyclohexyl-N-[2-(3hydroxy-phenyl)-ethyl]-acrylamide

To a stirred solution of the oil isolated in Step E (313 mg, 1.4 mmol) in methylene chloride (10 mL) and saturated aqueous sodium bicarbonate solution (10 m) at 0° C. was added acryloyl chloride (115 μL, 1.4 mmol). The resulting mixture was stirred for 1 h and then was extracted with methylene chloride. The solution was concentrated, the resulting residue was dissolved in MeOH (3 mL) and aqueous LiOH solution (1N, 1 mL). The mixture was then stirred at room temperature for 30 minutes. The solution was acidified with 1N HCl and then extracted with methylene chloride. The solution was dried over sodium sulfate and concentrated to yield an oil.

MH+=274

Step G: 6-Cyano-5-cyclohexyl-7-(5-fluoro-2-nitro-phenyl)-hepta-2,6-dienoic acid cyclohexyl-[2-(3-hydrixy-phenyl)-ethyl]-amide A stirred solution of the product isolated in Step C (0.96 g, 2.9 mmol), the oil isolated in Step F (1.18 g, 4.35 mmol), and Grubbs-Hoveyda ruthenium catalyst (100 mg) in dichloromethane (8 mL) under an nitrogen atmosphere was heated at 50° C. Additional ruthenium catalyst (200 mg) was added during the course of reaction until it was complete. The resulting solution washed with water and then dried over sodium sulfate. The crude product was purified by silica gel column chromatography elution with methylene chloride:methanol:ammonium hydroxide (100:1:0.1 to 100:2:0.2) to yield an oil.

MH+=574

Step H: 6-Cyano-5-cyclohexyl-7-(5-fluoro-2-nitro-7-phenyl)-hepta-2,6-dienoic acid cyclohexyl-[2-(3-hydroxy-phenyl)-ethyl]-amide A mixture of the oil isolated in Step G (0.8 g, 1.4 mmol) and cesium carbonate (0.91 g, 2.8 mmol) in DMF (15 mL) was heated at 50° C. for 2.5 h under an argon atmosphere. The resulting reaction mixture was poured into water (15 mL) and then extracted into ethyl acetate (100 mL). The organic solution washed with water (3×10 mL), NaCl solution (10 mL) and then dried over sodium sulfate. The solvent was removed to yield an oil.

MH+=554

Step I

To a solution of the oil isolated in Step H (0.8 g, 1.5 mmol) in methanol (30 mL) under argon was added zinc (200 mg) and ammonium chloride (240 mg). The resulting mixture was then heated at 80° C. Six additional portions of Zn (200 mg each time) and ammonium chloride (240 mg) were added every 6-10 h. The solid was filtered off, and the filtrate was concentrated to yield crude product. The crude product was purified by silica gel column chromatography elution with methylene chloride:methanol:ammonium hydroxide (100:2:0.2) to 100:3:0.3) to yield the title compound as an oil. The oil was dissolved in an isopropyl alcohol-water mixture and was treated with one equivalent of 0.2 N HCl and then lyophilized to yield the title compound as its corresponding colorless HCl salt.

MH+=524

¹H NMR (300 MHz, DMSO) δ 0.62-1.83 (m, 21 H), 2.62 (br, 2H), 2.75-2.90 (m, 1 H), 3.18-3.25 (br m, 1 H) 3.30-3.50 (br m, 3H), 3.5-3.6 (br s, 1 H), 6.1-6.25 (m, 1 H), 6.36-6.5 (m, 1 H), 6.9-7.1 (m, 2H), 7.3-7.4 (t, 1 H), 7.55-7.60 (d, 1 H), 7.75 (d, 1 H), 8.0 (s, 1 H), 8.5 (br s, 2H).

EXAMPLE 7

Compound #40

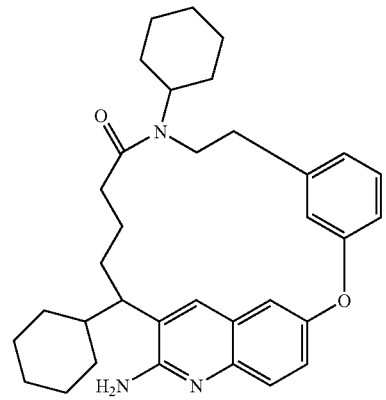

A mixture of the Compound prepared as in Example 6 above (36 mg) and Pd/C (10 mg) in ethanol (5 mL) was hydrogenated under 1 atmosphere of hydrogen over 12 h. The catalyst and solvent were removed, and the resulting residue was purified by silica gel column chromatography eluting with methylene chloride:methanol:ammonium hydroxide (100:2:02 to 100:3:0.3) to yield an oil. The oil was taken up in isopropyl alcohol-water and treated with one equivalent of 0.2 N HCl and then lyophilized to yield the title compound as its corresponding colorless HCl salt.

MH+=526

¹H NMR (300 MHz, DMSO) δ0.95-2.30 (m, 23H), 2.68-2.80 (m, 2H), 3.15-3.5 (m, 4H), 6.8 (d, 1 H), 7.05 (d, 1 H), 7.18 (s,1 H), 7.25 (d, 1 H), 7.55 (d, 1 H), 7.75 (s, 1 H), 7.8 (d, 1 H), 8.25 (s, 1 H), 8.40 (s, 2H).

EXAMPLE 8

Compound #41

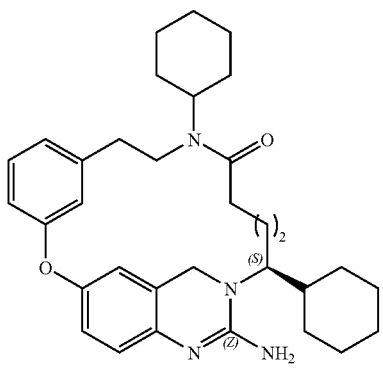

The title compound was prepared according to the procedure as described in Example 2 above, selecting and substituting suitably substituted reagents.

EXAMPLE 9

Compound #19

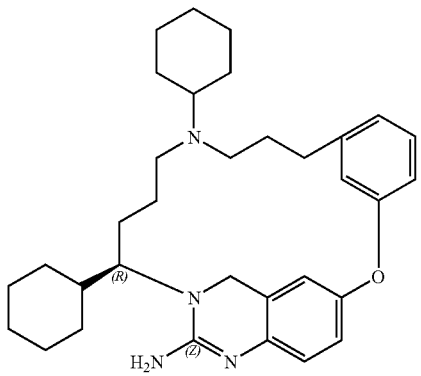

To a stirred solution of the Compound #41, prepared as in Example 8 above, (0.0458 g, 0.087 mmol) in THF (5.0 mL), borane in THF (1 M, 0.173 mL, 0.173 mmol) was added. The resulting solution was refluxed for 48 h. After cooling to room temperature, hydrochloric acid (1.0 M, 0.5 mL) was added to the reaction mixture. The resulting solution was concentrated to a residue and the residue was purified over Gilson HPLC to yield the title compound as a white solid, as its corresponding TFA salt.

MH$^+$=515.2

$^1$H NMR (300 MHz, DMSO) δ11.52 (s, 1H), 6.87-7.33 (m, 7H), 2.60-4.10 (br m,12H), 0.60-1.90 (m, 27H)

EXAMPLE 10

[2-(2-Amino-6-bromo-4H-quinazolin-3-yl)-ethyl]-carbamic acid tert-butyl ester

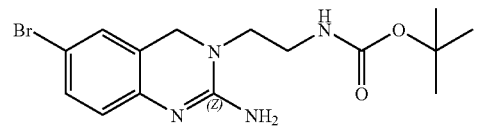

Step A:

To a single-neck 1-L round bottom flask was charged concentrated sulfuric acid (440 mL). The flask was chilled in an ice-water bath, and potassium nitrate (57.3 g, 0.567 mol) was added slowly in one portion, and the reaction mixture was stirred for 10 min. 3-Bromobenzaldehyde (100 g, 0.540 mol) was then added over a 15 min period, and the reaction mixture was stirred in the ice-water bath for 45 min. The reaction mixture was poured onto 2 L of crushed ice, and the ice was allowed to melt while stirring. The aqueous slurry was extracted with dichloromethane (3×400 mL), and the combined organic phases were washed with brine (200 mL), dried (MgSO$_4$), and concentrated in vacuo to yield a solid (a mixture of the desired product as well as other nitration isomers). The solid was split into two portions, and each portion was dissolved in dichloromethane/heptane (2:1, 400 mL) and loaded onto a Biotage 75 L (800 g silica gel) column. The columns were eluted with heptane (2 L) and 1:19 ethyl acetate-heptane (10 L) to yield a solid.

mp 69-71° C.

Elemental analysis for C$_7$H$_4$BrNO$_3$:

Calculated: % C 36.55, % H 1.74, % N 6.09, % Br 34.74

Found: % C 36.68, % H 1.68, % N 5.88, % Br 35.01

HPLC: R$_f$=3.273 min; ABZ+PLUS, 3 μm, 2.1×50 mm. Gradient: A=water (0.1% TFA), B=MeCN (0.1% TFA) @ 0.75 mL/min. Initial: A:B, 90:10. t=0.00-4.00 min (A:B, 10:90), t=4.00-4.10 min (A:B, 0:100), t=4.10-6.00 min (A:B, 0:100).

Step B:

A three-neck 2 L round bottom flask was charged with the solid prepared in Step A above (30 g, 0.130 mol), 2-(aminoethyl)-carbamic acid tert-butyl ester (20.9 g, 0.130 mol), and DCE (700 mL). The reaction mixture was stirred for 1 h, and then NaBH(OAc)$_3$ (68.9 g, 0.325 mol) was added. The reaction mixture was heated at 40° C. (exotherm observed, 47° C.) for 3.5 h. The reaction mixture was then cooled to 30° C. and quenched with 3M sodium hydroxide (exotherm observed, 39° C.). The reaction mixture was diluted with water (500 mL), and the layers were separated. The aqueous phase was extracted with dichloromethane (3×400 mL), and the combined organic phases were dried (MgSO$_4$) and concentrated in vacuo to yield crude product as a residual oil. The residual oil was dissolved in 1:2 heptane-dichloromethane (400 mL) and loaded onto a Biotage 75 L column (800 g silica gel). The column was eluted with heptane (4 L), then ethyl acetate-heptane, 1:9 (2 L), 1:4 (4 L), 2:3 (2 L), and 1:1 (4 L) to yield first an unidentified by-product followed by the desired product as an oil that solidified to a yellow solid upon standing.

mp 43-46° C.

Mass spectrum (Electrospray, positive mode): m/z=373/375 (M$^+$)

HPLC: $R_t$=2.321 min; ABZ+PLUS, 3 µm, 2.1×50 mm. gradient: A=water (0.1% TFA), B=MeCN (0.1% TFA) @ 0.75 mL/min. initial: A:B, 90:10. t=0.00-4.00 min (A:B, 10:90), t=4.00-4.10 min (A:B, 0:100), t=4.10-6.00 min (A:B, 0:100)

Step C:

A 2 L Parr shaker bottle was charged with a slurry of 3.0 g of 5% platinum (sulfided) on carbon in tetrahydrofuran (25 mL) followed by a solution of the yellow solid prepared in Step B above (27.9 g, 74.5 mmol) in THF (600 mL). The bottle was agitated under hydrogen gas (20-25 psi) for 5 h. The system required frequent re-pressurization during the initial 30 minutes of the reaction. The catalyst was removed by filtration through Celite®, and the filtrate was concentrated to yield a residue. The residue was used without further purification.

Mass Spectrum (Electrospray, positive mode): m/z=343/345 (M⁺)

HPLC: $R_t$=2.426 min; ABZ+PLUS, 3 µm, 2.1×50 mm. Gradient: A=water (0.1% TFA), B=MeCN (0.1% TFA) @ 0.75 mL/min. Initial: A:B, 90:10. t=0.00-4.00 min (A:B, 10:90), t=4.00-4.10 min (A:B, 0:100), t=4.10-6.00 min (A:B, 0:100)

Step D:

A 3 L one-necked flask equipped with magnetic stirrer and a nitrogen inlet was charged with the residue prepared in Step C above (26 g, 75.5 mmol) in EtOH (600 mL). The reaction mixture was cooled in an ice bath and a solution of cyanogen bromide in CH₃CN (5M, 15.1 mL, 75.5 mmol) was added in one portion. The reaction mixture was warmed to room temperature, stirred for 4 days and then brought to reflux for 3 h. The reaction mixture was cooled to room temperature, poured into water (1.2 L), basified with 3M aqueous sodium hydroxide, and stirred in an ice-water bath for 2 h. The resulting solid was collected by filtration, washed with 1:9 water:EtOH (250 mL), and dried to yield the title compound as a solid.

mp 199-205° C., decomp.

Mass spectrum (Electrospray, positive mode): m/z=368/370 (M⁺)

Elemental analysis: ($C_{15}H_{21}BrN_4O_2$):

Calc'd: % C 48.79, % H 5.73, % N 15.17, % Br 21.64
Found: % C 49.63, % H 5.81, % N 15.30, % Br 21.22
Karl-Fisher: 0.14% (w/w) water HPLC: $R_t$=7.967 min; Agilent Eclipse XDB-C8, 5 µm, 4.6×150 mm. Gradient: A=water (0.1% TFA), B=MeCN (0.1% TFA) @ 1.0 mL/min. Initial: A:B, 90:10. t=0.00-0.50 min (A:B, 90:10), t=0.50-11.50 min (A:B, 5:95), t=11.50-12.50 min (A:B, 5:95)

To the resulting residue in dichloromethane (2.5 mL) was added triethylamine (0.68 mL, 4.86 mmol), 5-hexenoic acid (92 mg, 0.81 mmol), and 2-chloro-1,3-dimethylimidazolinium chloride (150 mg, 0.89 mmol). The reaction mixture was stirred at room temperature for 16 h, and then concentrated to yield a residue.

Step B. Hex-5-enoic acid {2-[2-amino-6-(2-vinyl-phenyl)-4H-quinazolin-3-yl]-ethyl}-amide To the residue from step A in ethanol (3 mL) was added potassium carbonate (223 mg, 1.62 mmol) in water (0.6 mL), 2-vinylphenylboronic acid (180 mg, 1.22 mmol), and [1,1'-bis(diphenylphosphino)ferrocene]dichloropalladium(II) (33 mg, 0.04 mmol). The resulting mixture was irradiated (µwave) at 120° C. for 6 min and then concentrated in vacuo. The residue was taken up in ethyl acetate (2.4 mL) and water (1 mL). The solution was adsorbed onto diatomaceous earth and eluted with 1% triethylamine:ethyl acetate. The eluate was concentrated to a residue which was purified by reversed-phase chromatography to yield the corresponding TFA salt as a residue.

MS m/z (M+H)⁺ calculated for $C_{24}H_{29}N_4O$ 389.2, measured as 388.9.

STEP C:

A solution of the residue (28 mg, 0.06 mmol) isolated in Step B in dichloromethane (5 mL) was bubbled with nitrogen for 5 min, then tricyclohexylphosphine[1,3-bis(2,4,6-trimethylphenyl)-4,5-dihydroimidazol-2-ylidene][benzylidine] ruthenium (IV) dichloride (4.8 mg, 0.006 mmol) was added. The resulting mixture was evacuated and filled with nitrogen (3×), then irradiated (µwave) at 110° C. for 10 min. After cooling to room temperature, additional tricyclohexylphosphine[1,3-bis(2,4,6-trimethylphenyl)-4,5-dihydroimidazol-2-ylidene][benzylidine]ruthenium (IV) dichloride (4.8 mg, 0.006 mmol) was added and the reaction mixture was again irradiated (µwave) at 110° C. for 10 min. The resulting mixture was concentrated and the residue was purified by reversed-phase chromatography to yield the title compound as its corresponding TFA salt, as a residue.

¹H NMR (methanol-d₄): δ7.43 (d, 1H, J=7.6 Hz), 7.30-7.21 (m, 3H), 7.18 (d, 1H, J=7.6 Hz), 7.04 (d, 1H, J=8.0 Hz), 6.97 (s, 1H), 6.17 (d, 1H, J=16.2 Hz), 5.98 (m, 1H), 4.52 (br, 2H), 3.84-3.36 (m, 4H), 1.65 (br, 2H)

MS m/z (M+H)⁺ calculated for $C_{22}H_{25}N_4O$ 361.2, measured as 361.0

EXAMPLE 11

EXAMPLE 12

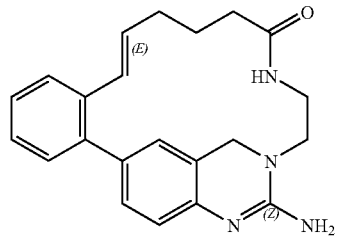

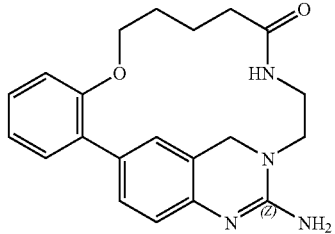

Step A: Hex-5-enoic acid [2-(2-amino-6-bromo-4H-quinazolin-3-yl)-ethyl]-amide

A mixture of [2-(2-amino-6-bromo-4H-quinazolin-3-yl)-ethyl]-carbamic acid tert-butyl ester (300 mg, 0.81 mmol) and trifluoroacetic acid (6 mL, 50% solution in dichloromethane) was stirred at 40° C. for 2 h and then concentrated in vacuo.

Step A. 5-Chloro-pentanoic acid [2-(2-amino-6-bromo-4H-quinazolin-3-yl)-ethyl]-amide A mixture of [2-(2-amino-6-bromo-4H-quinazolin-3-yl)-ethyl]-carbamic acid tert-butyl ester (266 mg, 0.72 mmol) and trifluoroacetic acid (5 mL, 50% solution in dichloromethane) was stirred at 40° C. for 2 h and then concentrated in vacuo.

To the resulting residue in dichloromethane (2 mL) was added triethylamine (0.5 mL, 3.6 mmol), 5-chlorovaleric acid (98 mg, 0.72 mmol), and 2-chloro-1,3-dimethylimidazolinium chloride (134 mg, 0.79 mmol) in dichloromethane (0.5 mL). The resulting mixture was stirred at room temperature for 16 h, and then concentrated in vacuo to yield a residue.

Step B. 5-Chloro-pentanoic acid {2-[2-amino-6-(2-hydroxyphenyl)-4H-quinazolin-3-yl]-ethyl}-amide To the residue from step A in ethanol (1 mL) was added potassium carbonate (66 mg, 0.48 mmol) in water (0.2 mL), 2-hydroxyphenylboronic acid (50 mg, 0.36 mmol), and [1,1'-bis(diphenylphosphino)ferrocene]dichloropalladium(II) (10 mg, 0.01 mmol). The resulting mixture was irradiated (μwave) at 120° C. for 6 min and then concentrated in vacuo. The residue was taken up in ethyl acetate (2.4 mL) and water (1 mL). The solution was absorbed onto diatomaceous earth and eluted with 1% triethylamine/ethyl acetate. The eluate was concentrated to a residue which was purified by reversed-phase chromatography to yield the corresponding TFA salt as a residue.

MS m/z (M+H)$^+$ calculated for $C_{21}H_{26}ClN_4O_2$ 401.2, measured as 400.9.

STEP C:

To a solution of the residue isolated in Step B (11 mg, 0.027 mmol) in dimethylformamide (1 mL) was added potassium carbonate (4 mg, 0.030 mmol). The reaction mixture was stirred at 80° C. for 16 h. The resulting mixture was then concentrated and the residue was purified by reversed-phase chromatography to yield the title compound as its corresponding trifluoroacetate salt, as a residue.

$^1$H NMR (DMSO-d$_6$): δ10.92 (s, 1H), 8.09 (m, 1H), 8.03 (s, 2H), 7.31 (m, 1H), 7.27 (m, 3H), 7.13 (d, 1H, J=8.2 Hz), 7.04 (m, 2H), 4.44 (s, 2H), 3.98 (m, 2H), 3.67 (m, 2H), 3.24 (m, 2H), 1.98 (m, 2H), 1.62 (br, 4H)

MS m/z (M+H)$^+$ calculated for $C_{21}H_{25}N_4O_2$ 365.2, measured as 365.0

Additional compounds of the present invention were similarly prepared according to the procedures and schemes described herein, selecting and substituting suitably substituted reagents and starting materials.

EXAMPLE 13 in vitro BACE FS1% Inhibition Assay

The following reagents were used in this assay: sodium acetate, PEG8000 (Sigma), DMSO, HEPES, FS1 substrate [R(AedensE)EEVNLDAEFK-(DabcylK)R], β-secretase (BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The FS1-substrate stock solution was prepared in DMSO as a 10 mg/mL solution. The FS1-substrate working solution was prepared by diluting the 10 mg/mL stock solution with substrate assay buffer to a final concentration of 300 μg/mL. The α-secretase (BACE) working solution was prepared by diluting a 0.83 mg/mL BACE stock solution with enzyme assay buffer to a final concentration of 4 μg/mL.

Test compounds were dissolved in DMSO to 10 mM. Compounds were further diluted in vehicle to various concentrations in the range of 405 μM to 4.05 μM (13.5× final compound concentration in screening plate).

The screening procedure for this assay was as follows: 15 μL of BACE working solution was pipetted into each well of a 96-well plate. To each well was then pipetted 2 μL of test compound at the selected concentration. Test compound and BACE were then mixed with a pipettor and incubated for 20 min at room temperature. To each well was then added 10 L of the FS1 substrate working solution. The plates were then incubated for 1 hour at room temperature. The fluorescence for each well was then measured on an LJL analyst (Ex 360 nm/Em 530 nm).

The procedure for the blank (negative control) was as follows. 15 μL of assay buffer was pipetted into each well to be used as a blank control. To each well was then added 2 μL of vehicle and 10 μL of FS1-substrate working solution. The plates were then incubated for 1 hour at room temperature. The fluorescence was measured on an LJL analyst (Ex 360 nm/Em 530 nm).

The procedure for the positive control was as follows: 15 μL of BACE working solution was pipetted into each well to be used as a positive control. To each well was then pipetted 2 μL of vehicle. Vehicle and BACE were then mixed with a pipettor and incubated for 20 min at room temperature. To each well was then added 10 μL of the FS1 substrate working solution. The plates were then incubated for 1 hour at room temperature. The fluorescence (Fl) was then measured on an LJL analyst (Ex 360 nm/Em 530 nm).

For test compounds, % inhibition was determined at each concentration as follows:

$$\% \text{ Inhibition} = \left[1 - \left(\frac{[Fl(\text{compound}) - Fl(\text{negative control})]}{[Fl(\text{positive control}) - Fl(\text{negative control})]}\right)\right] \times 100\%$$

% Inhibition values of less than 30% were indistinguishable from control and are listed as ≦30% in the Table below. % Inhibition values greater than 100% were indistinguishable from 100% within the error of the measurement.

EXAMPLE 14 in vitro BACE Assay

The following reagents were used in this assay: sodium acetate, PEG8000 (Sigma), DMSO, HEPES, FS1 substrate [R(AedensE)EEVNLDAEFK-(DabcylK)R], β-secretase (BACE) (Panvera), and 96-well plate (HE microplate, Molecular Devices).

The following assay buffers were prepared and used in this assay: (1) enzyme assay buffer (0.05 M sodium acetate, pH5, 0.1% PEG8000 (w/v)), (2) substrate assay buffer (0.05 M sodium acetate, pH5), and (3) compound vehicle (30% DMSO in 50 mM HEPES, pH 7.4).

The FS1-substrate stock solution was prepared in DMSO as a 10 mg/mL solution. The FS1-substrate working solution was prepared by diluting the 10 mg/mL stock solution with substrate assay buffer to a final concentration of 300 μg/mL. The β-secretase (BACE) working solution was prepared by diluting a 0.83 mg/mL BACE stock solution with enzyme assay buffer to a final concentration of 4 μg/mL.

Test compounds were dissolved in DMSO at 10 mM. Compounds were further diluted in compound vehicle to various concentrations in the range of 675 μM to 13.5 nM (13.5× final compound concentration in Ki plate).

The procedure for this assay was as follows: 15 μL of BACE working solution was pipetted into each well of a 96-well plate. To each well was then pipetted 2 μL of test compound at the selected concentration. Test compound and BACE were then mixed with a pipettor and incubated for 20 min at room temperature. To each well was then added 10 µL of the FS1 substrate working solution. The fluorescence for each well was then measured on a Polarstar fluorometer (Ex 390 nm/Em 520 nm) for 20 min at room temperature, reading fluorescence at 1 min intervals.

The procedure for the positive control was as follows: 15 µL of BACE working solution was pipetted into each well to be used as a positive control. To each well was then pipetted 2 µL of vehicle. Vehicle and BACE were then mixed with a pipettor and incubated for 20 min at room temperature. To each well was then added 10 µL of the FS1 substrate working solution. The fluorescence was then measured on a Polarstar fluorometer (Ex 390 nm/Em 520 nm) for 20 min at room temperature, reading fluorescence at 1 min intervals.

For test compounds, $K_i$ inhibition was determined as follows: For each compound concentration and positive control, rate of cleavage of substrate ($V_i$, where i=compound concentration in µM) was determined as $\Delta$ Fluorescence/$\Delta$ time (min). Cleavage rates ($V_i$) were plotted as a function of inhibitor concentration in µM [I]. The $K_i$ was then determined by fitting the following equation to the graph of [I] vs. $V_i$ $$Y = aV_{max}/(50 + 24*(1 + X/K_i)),$$

where 50=substrate concentration (µM) and 24=$K_m$ of substrate (µM).

Representative compounds of the present invention were tested according to procedures described in Examples 13 and 14 above, with results as listed in Table 4, below. Because the % Inhibition assay detects changes in fluorescence, negative values are possible. % Inhibition values of less than about 25% (including negative values) are within the noise or error of the procedures as described.

TABLE 4

BACE in vitro Assay

| ID No | % Inhibition (Example 13) | | | (Example 14) |
|---|---|---|---|---|
| | @ 3 µM | @ 1 µM | @ 0.3 µM | Ki (µM) |
| 1 | 117 | 105 | 74 | 0.051, 0.031 |
| 2 | 122, 123 | 127, 116 | 114, 116 | 0.039, 0.018, 0.0057 |
| 3 | 29 | 7 | 9 | |
| 4 | 120 | 115 | 100 | 0.044 |
| 5 | 43 | −6 | 3 | |
| 6 | 122 | 121 | 65 | 0.19 |
| 7 | 37 | 36 | 39 | |
| 8 | 51 | 49 | 8 | |
| 9 | 1 | −21 | −26 | |
| 10 | 7 | 5 | −9 | |
| 11 | 65 | 23 | −12 | |
| 12 | 11 | −0.4 | −18 | |
| 13 | 139 | 142 | 138 | 0.0079 |
| 14 | 139 | 138 | 117 | 0.017 |
| 15 | 10 | −31 | −36 | |
| 16 | 61 | 37 | 39 | |
| 17 | 151 | 145 | 139 | 0.0076 |
| 18 | 115 | 107 | 95 | 0.012 |
| 19 | 93 | 55 | 35 | 0.40 |
| 20 | 135 | 131 | 121 | 0.022 |
| 21 | 110 | 88 | 54 | 0.10 |
| 22 | 83 | 48 | 25 | 0.75 |
| 23 | 114 | 108 | 106 | 0.013 |
| 24 | 77 | 43 | 27 | 0.42 |
| 25 | 111 | 99 | 65 | 0.044 |
| 26 | 58 | 23 | −8 | |
| 27 | 117 | 117 | 106 | 0.011 |
| 28 | 110 | 59 | 4 | |
| 29 | 125 | 116 | 120 | 0.020 |
| 30 | 102 | 64 | 18 | |
| 31 | −15 | 16 | 14 | |
| 41 | 124 | 120 | 122 | 0.070 |

EXAMPLE 15 in vitro BACE Assay

This assay was run by CEREP (Catalog Ref. 761-B, Referred to SOP No. 1C131; ERMOLIEFF, J., LOY, J. A., KOELSCH, G. and TANG, J., Proteolytic activation of recombinant pro-memapsin 2 (pro-BACE) studied with new fluorogenic substrates, Biochemistry, (2000) Vol. 39, p. 12450).

More specifically the assay, run at 50 µL in a 96 well plate, evaluated the effect of test compound on the activity of the human BACE-1 quantified by measuring the formation of Mca-S-E-V—N-L-NH$_2$ from Mca-S-E-V—N-L-D-A-E-F—R—K(Dnp)-R—R—NH$_2$, using a recombinant enzyme.

The test compound, reference compound or water (control) was added to a buffer containing 0.09 M sodium acetate (pH 4.5) and 0.25 µg BACE-1. Compound interference with the fluorimetric detection method due to autofluorescence was then checked by measurements at the wavelengths defined to evaluate the enzyme activity. Thereafter, the reaction was initiated by adding 7.5 µM of the substrate Mca-S-E-V—N-L-D-A-E-F—R—K(Dnp)-R—R—NH$_2$ and the mixture was incubated for 60 min at 37° C. For control basal measurement, the substrate was omitted from the reaction mixture. Immediately after the incubation, the fluorescence intensity emitted by the reaction product Mca-S-E-V—N-L-NH$_2$ was measured at $\lambda$ex=320 nm and $\lambda$em=405 nm using a microplate reader (Ultra, Tecan). The standard inhibitory reference compound was OM99-2, which was tested in each experiment at several concentrations to obtain an inhibition curve from which its IC$_{50}$ value was calculated.

Representative compounds of the present invention were tested according to procedure described in Example 15 above with results as listed in Table 5 below.

TABLE 5

| ID No | % Inhibition and IC$_{50}$ | | |
|---|---|---|---|
| | 1 µM | 0.3 µM | IC$_{50}$ (µM) |
| 2 | | | 0.063 |
| 32 | | 99 | 0.055 |
| 33 | | 15 | |
| 34 | | 86 | 0.21 |
| 35 | | 93 | 0.083 |
| 36 | | 74 | 0.15 |
| 37 | | 100 | 0.07 |
| 38 | | 97 | 0.067 |
| 39 | 53 | | 0.81 |
| 40 | 13 | | |

Representative compounds of the present invention were further tested in various cellular assays. The measured results in these assays were generally consistent with the in vitro results listed above.

EXAMPLE 16

In Vivo Testing

Compounds of the present invention may be further tested for their effectiveness in the treatment of disorders mediated by the BACE enzyme, for example Alzheimer's disease, by testing the compounds in an in vivo assay, for example, as disclosed in Sirinathsinghji, D. J. S. (Merck Sharp and Dohme Research Laboratories, Neuroscience Research Centre, Essex, UK.), *Transgenic mouse models of Alzheimer's disease*, Biochemical Society Transactions (1998), 26 (3), pp 504-508;

Van Leuven, F. (Experimental Genetics Group, Center for Human Genetics, Flemish Institute for Biotechnology (VIB), K. U. Leuven, Louvain, Belg.), *Single and multiple transgenic mice as models for Alzheimer's disease*, Progress in Neurobiology (Oxford) (2000), 61 (3), pp 305-312;

Hsiao, K.; Chapman, P.; Nilsen, S.; Eckman, C.; Harigaya, Y.; Younkin, S.; Yang, F.; Cole, G. (Dep. Neurology, Univ. Minnesota, Minneapolis, Minn., USA), *Correlative memory deficits, Aβ elevation, and amyloid plaques in transgenic mice*, Science (Washington, D.C.) (1996), 274 (5284), pp 99-102 (Tg2576 mice);

Oddo, S.; Caccamo, A.; Shepherd, J. D.; Murphy, M. P.; Golde, T. E.; Kayed, R.; Metherate, R.; Mattson, M. P.; Akbari, Y.; LaFerla, F. M. (Department of Neurobiology and Behavior, University of California, Irvine, Irvine, Calif., USA), *Triple-transgenic model of Alzheimer's disease with plaques and tangles: Intracellular Aβ and synaptic dysfunction*, Neuron (2003), 39 (3), pp 409-421 (APP Triple Transgenic Mice);

Ruberti, F.; Capsoni, S.; Comparini, A.; Di Daniel, E.; Franzot, J.; Gonfloni, S.; Rossi, G.; Berardi, N.; Cattaneo, A. (Neuroscience Program, International School for Advanced Studies (SISSA), Trieste, Italy), *Phenotypic knockout of nerve growth factor in adult transgenic mice reveals severe deficits in basal forebrain cholinergic neurons cell death in the spleen, and skeletal muscle dystrophy*, Journal of Neuroscience (2000), 20 (7), pp 2589-2601 (AD11 mice);

Games, D.; Adams, D.; Alessandrini, R.; Barbour, R.; Berthelette, P.; Blackwell, C.; Carr, T.; Clemens, J.; Donaldson, T.; et al. (Athena Neurosciences, Inc., South San Francisco, Calif., USA), *Alzheimer-type neuropathology in transgenic mice overexpressing V717F β-amyloid precursor protein*, Nature (London) (1995), 373 (6514), pp 523-7 (V717F mice);

Neve, R. L.; Boyce, F. M.; McPhie, D. L.; Greenan, J.; Oster-Granite, M. L. (Dep. Genetics, Harvard Medical School and McLean Hospital, Belmont, Mass., USA), *Transgenic mice expressing APP-C100 in the brain*, Neurobiology of Aging (1996), 17 (2), pp 191-203 (APP-C100 mice);

and/or as disclosed in U.S. Pat. No. 5,811,633; U.S. Pat. No. 5,877,399; U.S. Pat. No. 5,672,805; U.S. Pat. No. 5,720,936; U.S. Pat. No. 5,612,486; U.S. Pat. No. 5,580,003; U.S. Pat. No. 5,850,003; U.S. Pat. No. 5,387,742; U.S. Pat. No. 5,877,015; U.S. Pat. No. 5,811,633; U.S. Pat. No. 6,037,521; U.S. Pat. No. 6,184,435; U.S. Pat. No. 6,187,922; U.S. Pat. No. 6,211,428; and U.S. Pat. No. 6,340,783.

EXAMPLE 17

Human Testing

Compounds of the present invention may be further tested for their effectiveness in the treatment of disorders mediated by the BACE enzyme, for example Alzheimer's disease, by testing the compounds in human subjects, for example, as disclosed in Lins, H.; Wichart, I.; Bancher, C.; Wallesch, C.-W.; Jellinger, K. A.; Roesler, N. (Department of Neurology, Otto-von-Guericke-University, Magdeburg, Germany), *Immunoreactivities of amyloid β peptide(1-42) and total τ protein in lumbar cerebrospinal fluid of patients with normal pressure hydrocephalus*, Journal of Neural Transmission (2004), 111 (3), pp 273-280;

Lewczuk, P.; Esselmann, H.; Otto, M.; Maler, J. M.; Henkel, A. W.; Henkel, M. K.; Eikenberg, O.; Antz, C.; Krause, W.-R.; Reulbach, U.; Kornhuber, J.; Wiltfang, J. (Department of Psychiatry and Psychotherapy, Molecular Neurobiology Lab, University of Erlangen-Nuremberg, Erlangen, Germany), *Neurochemical diagnosis of Alzheimer's dementia by CSF Aβ42, Aβ42/Aβ40 ratio and total tau*, Neurobiology of Aging (2004), 25 (3), pp 273-281;

Olsson, A.; Hoglund, K.; Sjogren, M.; Andreasen, N.; Minthon, L.; Lannfelt, L.; Buerger, K.; Moller, H.-J.; Hampel, H.; Davidsson, P.; Blennow, K. (Sahlgrenska University Hospital, Experimental Neuroscience Section, Institute of Clinical Neuroscience, Goteborg University, Moelndal, Sweden), *Measurement of α- and β-secretase cleaved amyloid precursor protein in cerebrospinal fluid from Alzheimer patients* Experimental Neurology (2003), 183 (1), pp 74-80;

Wahlund, L.-O.; Blennow, K. (Karolinska Institute, Section of Geriatric Medicine, Department of Clinical Neuroscience and Family Medicine, Huddinge University Hospital, Stockholm, Sweden), *Cerebrospinal fluid biomarkers for disease stage and intensity in cognitively impaired patients*, Neuroscience Letters (2003), 339 (2), pp 99-102;

El Mouedden, M., Vandermeeren, M., Meert, T., Mercken, M. (Johnson & Johnson Pharmaceutical Research and Development, Division of Janssen Pharmaceutica N.V., Turnhoutseweg 30, Beerse, Belg.), *Development of a specific ELISA for the quantitative study of amino-terminally truncated beta-amyloid peptides*, Journal of Neuroscience Methods (2005), 145 (1-2), pp 97-105;

Vanderstichele, H., Van Kerschaver, E., Hesse, C., Davidsson, P., Buyse, M.-A., Andreasen, N., Minthon, L., Wallin, A., Blennow, K., Vanmechelen, E., (Innogenetics N V, Ghent, Belg.), *Standardization of measurement of β-amyloid(1-42) in cerebrospinal fluid and plasma*, Amyloid (2000), 7 (4), pp 245-258;

and/or Schoonenboom, N. S., Mulder, C., Van Kamp, G. J., Mehta, S. P., Scheltens, P., Blankenstein, M. A., Mehta, P. D., *Amyloid β 38, 40, and 42 species in cerebrospinal fluid: More of the same?*, Annals of Neurology (2005), 58 (1), pp 139-142.

EXAMPLE 18

As a specific embodiment of an oral composition, 100 mg of the Compound #32, prepared as in Example 5 above, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

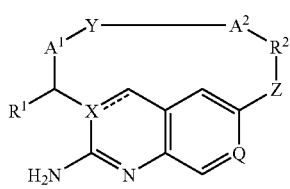

(I)

wherein
==== is a single or double bond;
X is —N—;
Q is =C(R⁴)—; wherein R⁴ is selected from the group consisting of hydrogen, halogen, $C_{1-4}$alkyl and $C_{1-4}$alkoxy;
R¹ is selected from the group consisting of hydrogen, $C_{1-8}$alkyl, hydroxy substituted $C_{2-8}$alkyl, $NR^A R^B$ substituted —$C_{2-8}$alkyl, —$C_{1-4}$alkyl-O—$C_{1-4}$alkyl, cycloalkyl, heterocycloalkyl, —($C_{1-4}$alkyl)-(cycloalkyl) and —($C_{1-4}$alkyl)- heterocycloalkyl); wherein $R^A$ and $R^B$ are each independently selected from the group consisting of hydrogen and $C_{1-4}$alkyl;
provided that when R¹ is hydroxy substituted $C_{2-8}$alkyl or $NR^A R^B$ substituted $C_{2-8}$alkyl, then the hydroxy or $NR^A R^B$ group is not bound to the alpha carbon;
A¹ is selected from the group consisting of —$C_{1-6}$alkyl- and —$C_{2-6}$alkenyl-;
Y is selected from the group consisting of —N(R³)—, —C(O)—N(R³)— and —N(R³)—C(O)—; provided that when X is =C— and Q is —C(R⁴)=, then Y is selected from the group consisting of —C(O)—N(R³)—;
wherein R³ is selected from the group consisting of hydrogen, $C_{1-8}$alkyl, —$C_{1-4}$alkyl-OH, $C_{3-8}$cycloalkyl, —($C_{1-5}$alkyl)-$C_{3-8}$cycloalkyl and 5 to 6 membered heterocycloalkyl; wherein the cycloalkyl or heterocycloalkyl is optionally substituted with one or more substituents independently selected from the group consisting of hydroxy, carboxy and —C(O)O—$C_{1-4}$alkyl;
A² is absent or is selected from the group consisting of —$C_{1-6}$alkyl-, —$C_{2-6}$alkenyl- and —$C_{1-6}$alkyl-O—;
R² is -phenyl;
Z is —O—;
or a pharmaceutically acceptable salt thereof.
2. A compound as in claim 1 wherein
==== is a single or double bond;
X is —N—;
Q is =C(R⁴)—; wherein R⁴ is selected from the group consisting of hydrogen, halogen, $C_{1-4}$alkyl and $C_{1-4}$alkoxy;
R¹ is selected from the group consisting of hydrogen, $C_{1-4}$alkyl, —$C_{1-4}$alkyl-O—$C_{1-4}$alkyl, cycloalkyl, —$C_{1-4}$alkyl-(cycloalkyl), saturated heterocycloalkyl and —$C_{1-4}$alkyl -(saturated heterocycloalkyl);
A¹ is selected from the group consisting of —$C_{1-4}$alkyl- and $C_{2-4}$alkenyl;
Y is selected from the group consisting of —N(R³)—, —C(O)—N(R³)— and —N(R³)—C(O)—; provided that when X is =C— and Q is —C(R⁴)=, then Y is selected from the group consisting of —C(O)—N(R³)—;
wherein R³ is selected from the group consisting of hydrogen, $C_{1-4}$alkyl, —$C_{1-4}$alkyl-OH, $C_{3-8}$cycloalkyl, —$C_{1-2}$alkyl-($C_{3-8}$cycloalkyl) and 5 to 6 membered, saturated heterocycloalkyl; wherein the cycloalkyl is optionally substituted with one to two substituents independently selected from hydroxy, carboxy or —C(O)O—$C_{1-4}$alkyl;
A² absent or is selected from the group consisting of —$C_{1-6}$alkyl-, $C_{2-6}$alkenyl and $C_{1-6}$alkyl-O—;
R² is selected from the group consisting of -phenyl-, -tetrahydronaphthyl- and -indanyl-;
Z is absent or is —O—;
or a pharmaceutically acceptable salt thereof.
3. A compound as in claim 2 wherein
==== is a single or double bond;
X is —N—;
Q is =C(R⁴)—; wherein R⁴ is selected from the group consisting of hydrogen, halogen and $C_{1-4}$alkoxy;
R¹ is selected from the group consisting of hydrogen, $C_{1-4}$alkyl, $C_{3-8}$cycloalkyl and 5 to 7 membered, saturated heterocycloalkyl;
A¹ is selected from the group consisting of —$C_{1-4}$alkyl- and $C_{2-4}$alkenyl;
Y is selected from the group consisting of —N(R³)—, —C(O)—N(R³)— and —N(R³)—C(O)—; provided that when X is =C— and Q is —C(R⁴)=, then Y is selected from the group consisting of —C(O)—N(R³)—;
wherein R³ is selected from the group consisting of hydrogen, —$C_{1-4}$alkyl-OH, $C_{5-7}$cycloalkyl, —$C_{1-2}$alkyl-($C_{3-8}$cycloalkyl) and 5 to 6 membered, saturated heterocycloalkyl; wherein the cycloalkyl is optionally substituted with a substituent selected from hydroxy, carboxy or —C(O)O—$C_{1-4}$alkyl;
A² absent or is selected from the group consisting of —$C_{1-4}$alkyl-, $C_{2-6}$alkenyl and $C_{1-4}$alkyl-O—;
R² is -phenyl-;
Z is —O—;
or a pharmaceutically acceptable salt thereof.
4. A compound as in claim 3, wherein
==== is a single or double bond;
X is —N—;
Q is =C(R⁴)—; wherein R⁴ is selected from the group consisting of hydrogen, fluoro and methoxy;
R¹ is selected from the group consisting of hydrogen, isopropyl, (R)-isopropyl, (S)-isopropyl, cyclohexyl, (S)-cyclohexyl, (R)-cyclohexyl, tetrahydropyranyl, (S) -tetrahydropyranyl and (R)-tetrahydropyranyl;
A¹ is selected from the group consisting of —$CH_2$—, —$CH_2CH_2$—, —$CH_2CH_2CH_2$— and —CH2—CH=CH—;
Y is selected from the group consisting of —N(cyclohexyl)- —C(O)—NH—, —C(O)—N(—$CH_2$-cyclopropyl)-, —C(O)—N(cyclopentyl)-, —C(O)—N(cyclohexyl)-, —C(O)—N(4-tetrahydropyranyl)-, —C(O)—N(1-(3-hydroxy-n-propyl))-, —C(O)—N(4-ethoxycarbonyl-cyclohexyl)-, —C(O)—N(4-carboxy-cyclohexyl)-, —C(O)—N(cis-4-carboxy-cyclohexyl)-, —C(O)—N(trans-4-carboxy-cyclohexyl)-, —C(O)—N(4-hydroxy-cyclohexyl)-, —C(O)—N(cis-4-hydroxy-cyclohexyl)-, —C(O)—N(trans-4-hydroxy-cyclohexyl)-, and —NH—C(O)—;
provided that when X is =C— and Q is —C(R⁴)=, then Y is selected from the group consisting of —C(O)—NH—, —C(O)—N(—$CH_2$-cyclopropyl)-, —C(O)—N(cyclopentyl)-, —C(O)—N(cyclohexyl)-, —C(O)—N(4-tetrahydropyranyl)-, —C(O)—N(1-(3-hydroxy-n- propyl))-, —C(O)—N(4-ethoxy-carbonyl-cyclohexyl)-, —C(O)—N(4-carboxy-cyclohexyl)-, —C(O)—N(cis-4-carboxy-cyclohexyl)-, —C(O)—N(trans-4-carboxy-cyclohexyl)-, —C(O)—N(4-hydroxy-cyclohexyl)-, —C(O)—N(cis-4-hydroxy-cyclohexyl)- and —C(O)—N(trans-4-hydroxy-cyclohexyl)-;

$A^2$ absent or is selected from the group consisting of —$CH_2$—, —$CH_2CH_2$—, —$CH_2CH_2CH_2$—, —$CH_2CH_2CH_2$—CH=CH—, —$CH_2CH_2$—O— and —$CH_2CH_2CH_2CH_2$—O—;

$R^2$ is selected from the group consisting of 1,2-phenyl, and 1,3-phenyl;

Z is —O—;

or a pharmaceutically acceptable salt thereof.

5. A compound as in claim 4, wherein

X is —N—;

Q is =C($R^4$)—; wherein $R^4$ is selected from the group consisting of hydrogen, fluoro and methoxy;

$R^1$ is selected from the group consisting of hydrogen, (S)-isopropyl, (S)-cyclohexyl, (R)-cyclohexyl and (S)-tetrahydropyranyl;

$A^1$ is selected from the group consisting of —$CH_2CH_2$— and —$CH_2CH_2CH_2$—;

Y is selected from the group consisting of —C(O)—NH—, —C(O)—N(cyclohexyl)-, —C(O)—N(4-tetrahydropyranyl)-, —C(O)—N(cis-4-hydroxy-cyclohexyl)-, —C(O)—N(trans-4-carboxy-cyclohexyl)- and —C(O—N(1-(3-hydroxy-n-propyl))-;

$A^2$ is selected from the group consisting of —$CH_2CH_2$—, —$CH_2CH_2CH_2$— and —$CH_2CH_2$—O—;

$R^2$ is 1,3-phenyl;

Z is —O—;

or a pharmaceutically acceptable salt thereof.

6. A compound as in claim 4, wherein

X is —N—;

Q is =CH—;

$R^1$ is selected from the group consisting of (S)-isopropyl, (S)-cyclohexyl and cyclohexyl;

$A^1$ is selected from the group consisting of —$CH_2CH_2$— and —$CH_2$—CH=CH—;

Y is selected from the group consisting of —C(O)—N(cyclopentyl)-, —C(O)—N(cyclohexyl)-, —C(O)—N(cis-4-carboxy-cyclohexyl)-, —C(O)—N(cis-4-hydroxy-cyclohexyl)- and —C(O)—N(—$CH_2$-cyclopropyl)-;

$A^2$ is absent or is —$CH_2CH_2$—;

$R^2$ is 1,3-phenyl;

Z is —O—;

or a pharmaceutically acceptable salt thereof.

7. A pharmaceutical composition comprising a pharmaceutically acceptable carrier and a compound of claim 1.

8. A process for making a pharmaceutical composition comprising mixing a compound of claim 1 and a pharmaceutically acceptable carrier.

* * * * *